United States Patent
Beck et al.

(10) Patent No.: US 9,017,296 B2
(45) Date of Patent: Apr. 28, 2015

(54) SAFETY OCCLUDER AND METHOD OF USE

(75) Inventors: Kent Beck, Layton, UT (US); Philip Eggers, Salt Lake City, UT (US); Jeff Juretich, Herriman, UT (US); Ryan Federspiel, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 708 days.

(21) Appl. No.: 12/415,966

(22) Filed: Mar. 31, 2009

(65) Prior Publication Data

US 2009/0254034 A1    Oct. 8, 2009

Related U.S. Application Data

(60) Provisional application No. 61/041,555, filed on Apr. 1, 2008.

(51) Int. Cl.
*A61M 5/00* (2006.01)
*A61M 39/28* (2006.01)

(52) U.S. Cl.
CPC ............ *A61M 39/284* (2013.01); *A61M 39/28* (2013.01); *A61M 39/281* (2013.01); *A61M 39/283* (2013.01)

(58) Field of Classification Search
CPC . A61M 39/281; A61M 39/28; A61M 39/284; A61M 39/286
USPC .......... 251/4, 7; 604/153, 249, 246, 247, 250, 604/251, 256, 30, 500, 537, 80, 34
See application file for complete search history.

(56) References Cited

U.S. PATENT DOCUMENTS

| | | | |
|---|---|---|---|
| 584,091 A | 6/1897 | Leidich | |
| 1,238,521 A | 8/1917 | Janish, Jr. | |
| 2,471,623 A | 5/1949 | Hubbell | |
| 2,518,165 A | 8/1950 | Millard | |
| 2,858,095 A | 10/1958 | Harris et al. | |
| 2,889,848 A * | 6/1959 | Redmer | 137/315.07 |
| 2,999,499 A | 9/1961 | Valet | |
| 3,213,882 A | 10/1965 | Beatty | |
| 3,329,391 A | 7/1967 | Deane | |
| D208,753 S | 9/1967 | Curry | |
| 3,497,175 A | 2/1970 | Koland | |
| 3,707,972 A | 1/1973 | Villari et al. | |
| 3,822,052 A * | 7/1974 | Lange | 251/10 |

(Continued)

FOREIGN PATENT DOCUMENTS

| | | |
|---|---|---|
| CN | 1795937 A | 7/2006 |
| EP | 0 150 666 | 9/1984 |

(Continued)

OTHER PUBLICATIONS

Written Opinion of the International Searching Authority and International Search Report, Nov. 16, 2009, by Tae San Kim.

*Primary Examiner* — Scott Medway
(74) *Attorney, Agent, or Firm* — Hodgson Russ LLP

(57) ABSTRACT

An improved safety occluder and method of use provides an occluder for an infusion set having a first, occluding position, a second, non-occluding position which returns to the first, occluding position when the occluder's plunger is released, and a third, non-occluding position which retains the plunger in a configuration which allows fluid flow through the infusion set. The occluder may also include a locking mechanism to prevent accidental movement of the plunger out of the first, occluding position.

24 Claims, 14 Drawing Sheets

(56) References Cited

U.S. PATENT DOCUMENTS

| | | | |
|---|---|---|---|
| 3,985,140 A | 10/1976 | Harris | |
| 3,998,364 A | 12/1976 | Hollander | |
| 4,037,596 A | 7/1977 | LeFevre et al. | |
| 4,063,555 A | 12/1977 | Ulinder | |
| 4,065,093 A | 12/1977 | Phillips | |
| 4,106,675 A | 8/1978 | Taylor | |
| 4,142,645 A | 3/1979 | Walton | |
| 4,146,018 A * | 3/1979 | Aldridge et al. | 600/498 |
| 4,160,383 A | 7/1979 | Rauschenberger | |
| 4,230,151 A | 10/1980 | Jonsson | |
| 4,236,880 A | 12/1980 | Archibald | |
| 4,373,524 A | 2/1983 | Leibinsohn | |
| 4,381,591 A | 5/1983 | Barger et al. | |
| 4,382,453 A | 5/1983 | Bujan et al. | |
| 4,425,116 A | 1/1984 | Bilstad et al. | |
| 4,430,073 A | 2/1984 | Bemis et al. | |
| 4,453,292 A * | 6/1984 | Bakker | 24/115 G |
| 4,453,295 A | 6/1984 | Laszczower | |
| 4,493,710 A * | 1/1985 | King et al. | 604/250 |
| 4,498,843 A | 2/1985 | Schneider et al. | |
| 4,524,802 A | 6/1985 | Lawrence et al. | |
| 4,527,588 A | 7/1985 | Tseo et al. | |
| 4,559,036 A | 12/1985 | Wunsch | |
| 4,559,045 A | 12/1985 | Danby et al. | |
| 4,579,553 A | 4/1986 | Urquhart et al. | |
| 4,586,691 A * | 5/1986 | Kozlow | 251/7 |
| 4,596,557 A | 6/1986 | Pexa | |
| 4,617,012 A * | 10/1986 | Vaillancourt | 604/29 |
| 4,624,663 A | 11/1986 | Danby et al. | |
| 4,634,092 A | 1/1987 | Daniell et al. | |
| 4,643,389 A * | 2/1987 | Elson et al. | 251/10 |
| 4,645,489 A | 2/1987 | Krumme et al. | |
| 4,689,043 A | 8/1987 | Bisha | |
| 4,724,584 A * | 2/1988 | Kasai | 24/115 G |
| 4,728,324 A | 3/1988 | Steigerwald et al. | |
| 4,730,635 A | 3/1988 | Linden | |
| 4,787,406 A | 11/1988 | Edwards et al. | |
| 4,794,673 A * | 1/1989 | Yamaguchi | 24/115 G |
| 4,800,920 A * | 1/1989 | Yusko et al. | 137/556 |
| 4,839,946 A * | 6/1989 | Murai | 24/115 G |
| 4,913,401 A | 4/1990 | Handke | |
| 4,932,629 A | 6/1990 | Rodomista et al. | |
| 4,932,938 A | 6/1990 | Goldberg et al. | |
| 4,935,010 A | 6/1990 | Cox et al. | |
| 4,960,259 A | 10/1990 | Sunnanvader et al. | |
| 5,017,192 A | 5/1991 | Dodge et al. | |
| 5,020,562 A | 6/1991 | Richmond et al. | |
| 5,022,422 A | 6/1991 | di Palma | |
| 5,083,561 A | 1/1992 | Russo | |
| 5,098,406 A | 3/1992 | Sawyer | |
| 5,149,318 A * | 9/1992 | Lindsay | 604/6.15 |
| 5,151,019 A | 9/1992 | Danby et al. | |
| 5,188,334 A | 2/1993 | Yoshii et al. | |
| 5,219,327 A | 6/1993 | Okada | |
| 5,232,193 A | 8/1993 | Skakoon | |
| 5,238,218 A | 8/1993 | Mackal | |
| 5,254,083 A | 10/1993 | Gentelia et al. | |
| 5,257,978 A | 11/1993 | Haber et al. | |
| 5,265,847 A | 11/1993 | Vorhis | |
| 5,300,044 A * | 4/1994 | Classey et al. | 604/250 |
| 5,323,514 A * | 6/1994 | Masuda et al. | 24/115 G |
| 5,336,174 A | 8/1994 | Daoud et al. | |
| 5,345,657 A * | 9/1994 | Shimizu | 24/115 G |
| 5,351,932 A | 10/1994 | Von Herrmann | |
| 5,361,461 A * | 11/1994 | Anscher | 24/115 G |
| 5,391,144 A | 2/1995 | Sakurai et al. | |
| 5,395,351 A | 3/1995 | Munsch | |
| 5,396,925 A | 3/1995 | Poli | |
| 5,437,642 A | 8/1995 | Thill et al. | |
| 5,453,098 A * | 9/1995 | Botts et al. | 604/249 |
| 5,474,544 A | 12/1995 | Lynn | |
| 5,482,446 A | 1/1996 | Williamson et al. | |
| 5,514,102 A | 5/1996 | Winterer et al. | |
| 5,531,713 A | 7/1996 | Mastronardi et al. | |
| 5,556,386 A | 9/1996 | Todd | |
| 5,567,120 A * | 10/1996 | Hungerford et al. | 417/63 |
| 5,578,070 A | 11/1996 | Utterberg | |
| 5,649,340 A * | 7/1997 | Ida | 24/115 G |
| D389,228 S | 1/1998 | Winterer et al. | |
| 5,704,584 A | 1/1998 | Winterer et al. | |
| 5,720,721 A | 2/1998 | Dumas et al. | |
| 5,737,808 A * | 4/1998 | Ikeda | 24/115 G |
| 5,807,312 A | 9/1998 | Dzwonkiewicz | |
| 5,810,323 A | 9/1998 | Winterer et al. | |
| 5,826,621 A | 10/1998 | Jemmott | |
| 5,967,484 A * | 10/1999 | Morris | 251/4 |
| 5,971,357 A | 10/1999 | Denton et al. | |
| 6,017,332 A | 1/2000 | Urrutia | |
| 6,048,331 A | 4/2000 | Tsugita et al. | |
| 6,092,695 A | 7/2000 | Loeffler | |
| 6,142,979 A | 11/2000 | McNally et al. | |
| 6,183,447 B1 | 2/2001 | Urrutia | |
| 6,196,922 B1 | 3/2001 | Hantschk et al. | |
| 6,196,992 B1 | 3/2001 | Keilman et al. | |
| 6,209,538 B1 | 4/2001 | Casper et al. | |
| 6,261,262 B1 | 7/2001 | Briggs et al. | |
| 6,361,016 B1 * | 3/2002 | Schulz | 251/7 |
| D455,489 S | 4/2002 | Beck et al. | |
| 6,398,758 B1 | 6/2002 | Jacobsen et al. | |
| 6,398,780 B1 | 6/2002 | Farley et al. | |
| 6,461,335 B1 | 10/2002 | Noecker | |
| 6,494,864 B1 | 12/2002 | Kerwin et al. | |
| 6,595,950 B1 | 7/2003 | Miles et al. | |
| 6,623,447 B2 | 9/2003 | Miles et al. | |
| 6,629,955 B2 * | 10/2003 | Morris et al. | 604/153 |
| H2090 H | 11/2003 | Walker | |
| 6,658,704 B2 * | 12/2003 | Buscart | 24/115 G |
| 6,685,670 B2 | 2/2004 | Miles et al. | |
| 6,749,591 B1 | 6/2004 | McNally et al. | |
| D503,978 S | 4/2005 | Beck | |
| 6,883,773 B1 | 4/2005 | Mattheis | |
| 6,923,785 B2 | 8/2005 | Miles et al. | |
| 6,942,473 B2 * | 9/2005 | Abrahamson et al. | 417/474 |
| 6,979,311 B2 | 12/2005 | Miles et al. | |
| 7,124,996 B2 * | 10/2006 | Clarke et al. | 251/7 |
| 7,150,727 B2 | 12/2006 | Cise et al. | |
| D556,904 S * | 12/2007 | Clarke | D24/129 |
| 7,367,963 B2 | 5/2008 | Cise et al. | |
| 7,682,368 B1 * | 3/2010 | Bombard et al. | 606/142 |
| 7,806,887 B2 * | 10/2010 | Raulerson et al. | 604/513 |
| D634,005 S * | 3/2011 | Beck | D24/129 |
| 7,938,444 B2 * | 5/2011 | Williams et al. | 280/743.2 |
| 2002/0127708 A1 | 9/2002 | Kluttz et al. | |
| 2002/0165503 A1 * | 11/2002 | Morris et al. | 604/250 |
| 2002/0169423 A1 * | 11/2002 | Zoltan et al. | 604/250 |
| 2002/0169424 A1 | 11/2002 | Miles et al. | |
| 2004/0220542 A1 | 11/2004 | Cise et al. | |
| 2004/0260332 A1 | 12/2004 | Dubrul et al. | |
| 2005/0119625 A1 | 6/2005 | Miles et al. | |
| 2006/0058740 A1 | 3/2006 | Cise et al. | |
| 2007/0265559 A1 | 11/2007 | Kunishige et al. | |
| 2008/0065008 A1 | 3/2008 | Barbut et al. | |
| 2008/0276911 A1 | 11/2008 | Woody | |

FOREIGN PATENT DOCUMENTS

| | | |
|---|---|---|
| EP | 0 276 356 | 8/1988 |
| EP | 0 423 978 | 10/1990 |
| EP | 0 483 794 | 10/1991 |
| EP | 1211445 | 6/2002 |
| GB | 2 338 759 | 12/1999 |
| WO | WO 96/08666 | 3/1996 |
| WO | WO 96-17636 | 6/1996 |

* cited by examiner

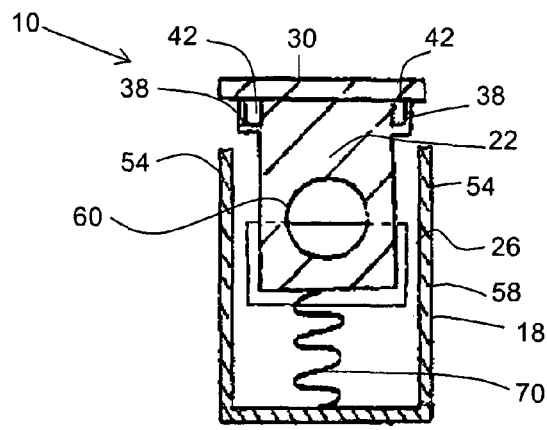 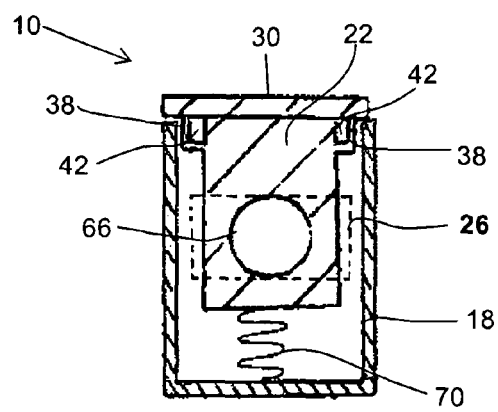
FIG. 5A  FIG. 5B
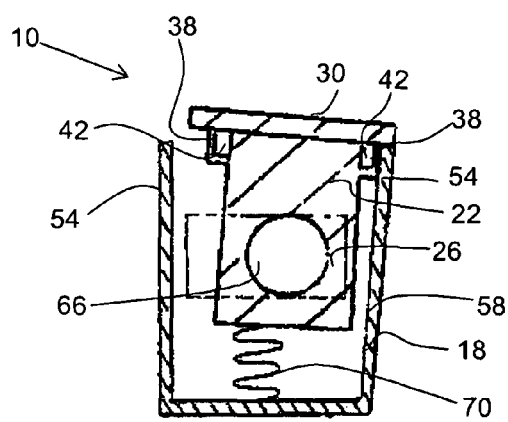 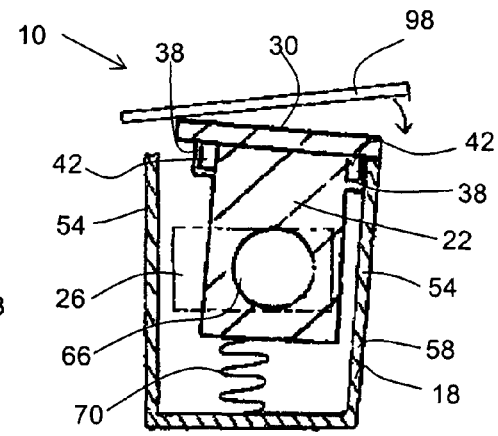
FIG. 5C  FIG. 5D

SAFETY OCCLUDER AND METHOD OF USE

RELATED APPLICATIONS

The present application claims the benefit of U.S. Provisional Application Ser. No. 61/041,555, filed Apr. 1, 2008, which is expressly incorporated herein in its entirety.

BACKGROUND OF THE INVENTION

1. The Field of the Invention

The present invention relates to an apparatus and method for selectively preventing free flow during enteral or parenteral administration of solutions through an infusion line. More particularly, the present invention relates to an occluder/valve and method of use for infusion sets and the like, wherein the occluder/valve prevents undesirable free-flow of solution through the infusion set while allowing a health care worker to place the infusion set in a free-flow condition to facilitate the rapid delivery of fluids to a patient.

2. State of the Art

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump or an IV pump, is placed along the infusion set to control the rate at which the solution is fed to the patient. In applications where a pump, etc., is used, the clamp used to regulate flow is typically opened to its fullest extent to prevent the clamp from interfering with the proper functioning of the pump. The clamp is opened with the expectation that the enteral feeding pump will control fluid flow through the infusion set. However, emergencies or other distractions may prevent the medical personnel from properly loading the infusion set in the enteral feeding pump.

When the infusion set is not properly loaded in the pump and the clamp has been opened, a situation known as free-flow often develops. The force of gravity causes the solution to flow freely into the patient unchecked by the pump or other regulating device. Under a free-flow condition, an amount of solution many times the desired dose can be supplied to the patient within a relatively short time period. This can be particularly dangerous if the solution contains potent medicines and the patient's body is not physically strong enough to adjust to the large inflow of solution. In fact, there have been numerous occasions in which the patient has died due to the over-infusion of fluid during a given amount of time. Thus, preventing an undesirable free-flow state is highly desirable.

Numerous devices have been developed in an attempt to prevent free flow conditions. Such devices, however, add to the overall cost of the infusion set and some provide only marginal protection against free flow. Others may have other limitations which limit the usefulness of the occluder.

One popular occluder is described in U.S. Pat. No. 5,704,584 (Winterer et al.). The '584 patent teaches an occluder which is disposed around the outside of an infusion set to selectively prevent fluid flow. The occluder is biased into a closed position wherein the occluder stops flow through the infusion set. The biasing can be overcome by manually holding the occluder open, or by mounting the occluder in a pump and then closing a door so that the door holds the occluder open.

An alternate to such an occluder is shown in U.S. Pat. No. 6,595,950 (Miles et al.). The '950 patent teaches an occluder which is disposed inside the infusion set to selectively block fluid flow from passing through the infusion set. The occluder disclosed in the '950 patent can be overcome either by applying force to the infusion set in such a manner as to open a passage between the wall of the infusion set and the occluder, or by applying sufficient pressure to the feeding or infusion solution to cause the infusion set to radially expand and open a flow channel past the occluder.

While preventing unintended free-flow situations is important, there are also times in which a free-flow condition is desired. This is particularly true when a patient's heart has stopped or other emergency situations. Often medicines will be injected into an IV solution being administered to the patient with the desire that the solution and medicine enter the patient as quickly as possible. If the infusion set uses one of the above referenced occluders, the medical staff must ensure that free-flow conditions are being allowed. This may mean removing the infusion set from the pump in which it is housed and manually holding open the occluder. It is typically not desirable that a person must hold the occluder open, as each member of the medical staff has important duties during an emergency situation. Thus, it is desirable for medical staff to be able to lock the occluder open in an emergency or other situation in which a free-flow condition is specifically desired.

Several occluders can be locked in an open position. For example, U.S. Pat. No. 4,634,092 (Daniell et al.) teaches an occluder which is biased closed. A pin may be inserted into a pair of apertures to hold the occluder in an open position. Such occluders, however, are disadvantageous because the pin can be lost during the commotion involved with an emergency and the occluder may be left in a biased closed condition.

Still another occluding system is shown in U.S. Pat. No. 5,257,978 (Haber et al.). The '978 patent shows a safety module in which a spring is biased to pinch closed tubing of an infusion set. The spring can be pushed into an open position where it allows flow through the infusion set by pressing down on a locking trigger. The locking trigger can also be moved into a locked position wherein the spring is held in an open position. The occluding system shown in the '978 patent is disadvantageous, as it is relatively bulky. Additionally, if the trigger is disposed in the locked open position, the module cannot be properly loaded into a pump, as the pump door will not close.

Thus, there is a need for a device having a default position that prevents a free-flow condition when not properly mounted in a pump, etc., while allowing controlled flow through the infusion set during normal use, and which also allows for a free-flow condition when desired by medical personnel. It is also desirable to provide such a device which is relatively inexpensive and easy to use.

SUMMARY OF THE INVENTION

It is an object of the present invention to provide an apparatus and method for selectively occluding infusion sets to prevent an accidental free-flow condition and which can be locked into a free-flow condition.

It is another object of the present invention to provide an occluder which is relatively simple to use.

The above and other objects of the invention are realized in an apparatus and method for preventing free flow in an infusion set. In accordance with one aspect of the invention, an occluder is disposed along the infusion set. The occluder is configured in a default position to prevent free flow of fluids in the infusion set past the occluder. The occluder is also configured, however, selectively to allow solutions to pass by the occluder which are pumped by an enteral feeding pump and the like either by the occluder being placed in a pump and the pump holding the occluder in an open position, or by medical personnel placing the occluder in a free-flow permitting position.

In accordance with one embodiment of the invention, the occluder is formed by a body which is placed along the tubing of an infusion set. The body includes a plunger which selectively engages the tubing of the infusion set to selectively squeeze closed the infusion set and thereby stop flow through the infusion set. The plunger also has a user adjustable engagement with the body which allows the plunger to be biased in a first, closed, occluding position when the plunger is in a first orientation.

The plunger can be moved into a second orientation by pressing down the plunger. In the second orientation, the plunger is in a second, open, non-occluding position, wherein the plunger does not interfere with the flow through the infusion set. The plunger may be placed in the second orientation by either manually pressing down on the plunger, or by mounting the occluder in a pump and using a pump door or other structure to hold the plunger in the non-occluding position.

The plunger can also be moved into a third orientation wherein the plunger is held in a third, open, non-occluding position. When the plunger is in the third orientation, the plunger is held in the third, open, non-occluding position so as to allow free-flow through the infusion set independent of whether the body is disposed in a pump or not and independent from the application of an external force to the plunger.

In accordance with one aspect of the invention, the plunger has a first path of movement wherein the plunger moves between the first, closed or occluding position and the second, open or non-occluding position and vice versa. In the first path of movement, application of force to the plunger will move the plunger into the second position and allow flow through the infusion set. Release of the force will allow the plunger to return to the first position and thereby occlude fluid flow through the infusion set.

The plunger also has a second path of movement between the second, open or non-occluding position and a third, open or non-occluding position. When the plunger is moved into the third position the plunger may move slightly along the second path of movement, but the plunger is held so that it will not occlude the infusion set tubing and inhibit flow therethrough.

In accordance with another aspect of the invention, the plunger and the body engage each other so that the plunger is biased into movement along the first path of movement. Thus, unless the plunger is affirmatively moved into the second path of movement, the plunger moves along the first path of movement and occludes flow through the infusion set by default.

Biasing of the plunger into the first path of movement can be accomplished by a biasing engagement between the body and the plunger. Thus, for example, a portion of the body may be deflected by movement of the plunger into the third position. When the plunger is in the third position, the portion of the body remains in a deflected state. When the plunger is moved toward the second position, the bias of the portion of the body to return to its normal position pushes against the plunger and encourages the plunger to move along the first path of movement. Thus, unless force is specifically applied to keep the plunger moving along the second path of movement, the plunger will return to the first path of movement and will move into the first occluding position as soon as external force is no longer being applied to the plunger.

As with prior art occluders, the plunger can be moved into the second position by the closing of a door or other structure of a pump such as an enteral feeding pump, an IV pump, etc. Additionally, the plunger can also be configured to be moved from the third position to the second position by the closing of a door, etc. Due to the biasing of the plunger into the first path of movement, opening of the door, etc., will allow the plunger to move back into the first position, thereby occluding flow through the infusion set. Thus, if medical personnel inadvertently mount the occluder into the pump with the occluder in the third position (i.e. locked open), closing the door will move the occluder out of the third position and will prevent the occluder from remaining in a free-flow condition in the event that the pump door is opened or the occluder is removed from the pump.

In accordance with another aspect of the invention, the occluder can also be locked open by insertion of a retaining pin if desired. A retaining pin may be used, for example, during shipment of the infusion set so that the occluder does not remain in a biased closed position and crease the infusion set tubing over a prolonged period of time.

In accordance with another aspect of the invention, the occluder includes a body and a plunger. The plunger is formed integrally with a biasing member for urging the plunger into the first, closed, occluding position. The plunger can be moved along a first path into the second, open, non-occluding position. The plunger can also be moved along a second path into a third, open, non-occluding position wherein the occluder is locked open until an external force moves the plunger back to the second position, where it will move along the first path of movement.

In accordance with still yet another aspect of the present invention, the occluder may be provided with a locking mechanism which prevents the plunger from being moved out of the first, closed or occluding position unless the locking mechanism is released to prevent accidental opening of the occluder. Thus, for example, the occluder could not be accidentally opened if a patient were to roll over on the occluder. However, medical personnel could readily over-ride the locking mechanism to allow flow past the occluder. Likewise, the pump could be configured to disengage the locking mechanism when the occluder is mounted in the pump.

These and other aspects of the present invention are realized in a safety occluder and method of use as shown and described in the following figures and related description.

BRIEF DESCRIPTION OF THE DRAWINGS

Various embodiments of the present invention are shown and described in reference to the numbered drawings wherein:

FIG. 5A shows a cross-sectional view of the occluder of FIG. 1 taken along the lines 5A-5A when the occluder is in a first, closed, occluding position;

FIG. 5B shows a cross-sectional view of the occluder of FIG. 1 taken along the lines 5A-5A when the occluder is in the second, open, non-occluding position;

FIG. 5C shows a cross-sectional view of the occluder of FIG. 1 taken along the lines 5A-5A when the occluder is in the third, open, non-occluding position;

FIG. 5D shows a cross-sectional view of a pump door engaging an occluder locked in the third, open or non-occluding position;

FIG. 5E shows a projection and channels from the plunger and body of the occluder when the plunger is in the first, closed, occluding position;

FIG. 5F shows a projection and channels from the plunger and body of the occluder when the plunger is in the second, open, non-occluding position;

FIG. 10A shows a perspective view of yet another alternate configuration of a safety occluder in a first, closed or occluding position;

FIG. 10B shows a side view of the safety occluder of FIG. 10A in the occluding position disposed along tubing of an infusion set;

It will be appreciated that the drawings are illustrative and not limiting of the scope of the invention which is defined by the appended claims. The various elements of the invention accomplish various aspects and objects of the invention. It is appreciated that not every element of the invention can be clearly displayed in a single drawing, and as such not every drawing shows each element of the invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
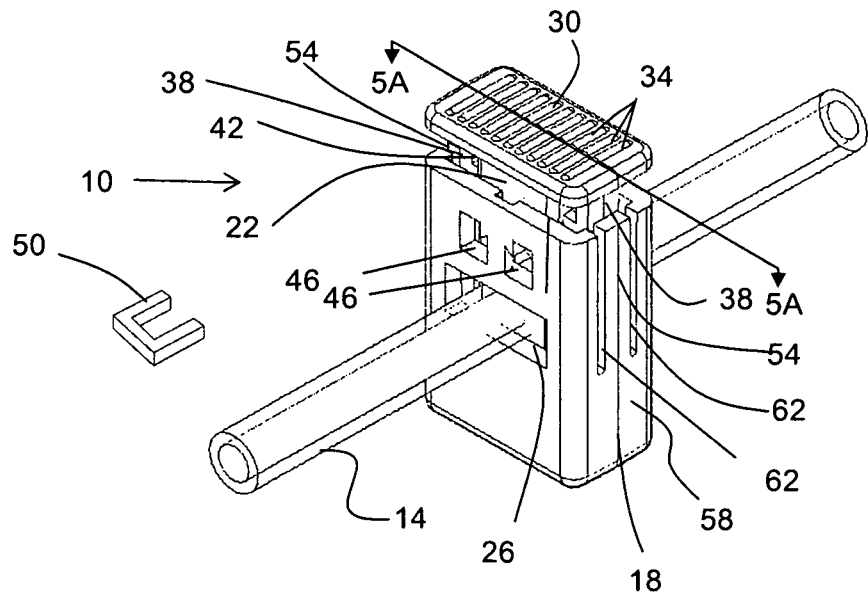
FIG. 1 shows a perspective view of a safety occluder made in accordance with the principles of the present invention in a first, closed, occluding position and disposed on a piece of tubing of an infusion set.

Turning to FIG. 1, there is shown a perspective view of an occluder, generally indicated at 10, disposed along a piece of tubing 14 of an infusion set 14. A short section of the tubing has been shown for clarity in the drawing. However, it will be appreciated that the tubing 14 will typically be connected to a solution reservoir at one end, and to an infusion adapter at an opposing end. The infusion adaptor may be an adaptor for connection to a stoma tube in the context of enteral feeding or an IV needle in the context of parenteral solutions.

The occluder 10 shown in FIG. 1 is in a first, closed or occluding position. The occluder 10 includes a body 18 and a plunger 22. The body 18 includes a void into which the plunger 18 is slidably positioned. The body 18 includes openings 26 on each side to receive the tubing 14 of the infusion set. The plunger 22 also includes a corresponding opening therethrough for receiving a portion of the tubing.

When the opening in the plunger 22 is not in alignment with the openings 26 in the body, the sidewall defining the opening in the plunger and an opposing sidewall defining the opening in the body will pinch closed the tubing 14 and prevent fluid to flow therethrough. In the configuration shown in FIG. 1, the sidewall defining the opening in the plunger 22 and the top sidewall defining the opening 26 in the body will engage opposing sides and thereby pinch the tubing closed.

As shown in FIG. 1, the plunger 22 includes a handling portion 30 disposed at the top thereof. The handling portion 30 includes a plurality of grooves, protrusions or other tactile features 34 to provide the user with a grip on the plunger. As will be explained in additional detail below, the handling portion 30 is used to pull the plunger 22 out of its normal path of travel between the first, closed or occluding position shown in FIG. 1 and a second, open or non-occluding position.

The plunger 22 also includes a pair of guides 38 which help center the plunger in the body 14. The guides 38 may include openings 42 which cooperate with openings 46 in the body 18 to receive a retaining pin 50 to hold the plunger in the second, open or non-occluding position. The pin 50 may be used, for example, during shipment of the infusion set to keep the plunger 22 and body 18 from creasing the tube 14.

The body 18 also includes a pair of guides 54 for encouraging the plunger 22 into a center position. The guides 54 are formed by a portion of the sidewall 58 of the body 18. A pair of slots 62 are formed in the sidewall 58 to form the guides 54. The guides 54 can be pivoted outwardly if lateral pressure is applied to the handling portion 30. However, the guides 54 are biased to return to their original position. Thus, unless the plunger 22 is affirmatively held to either side (either by a retention mechanism discussed below, or by the user applying force to the handling portion 30), the guides 54 will engage the guides 38 on the plunger 22 and center the plunger in the body 18.

Figure 2:
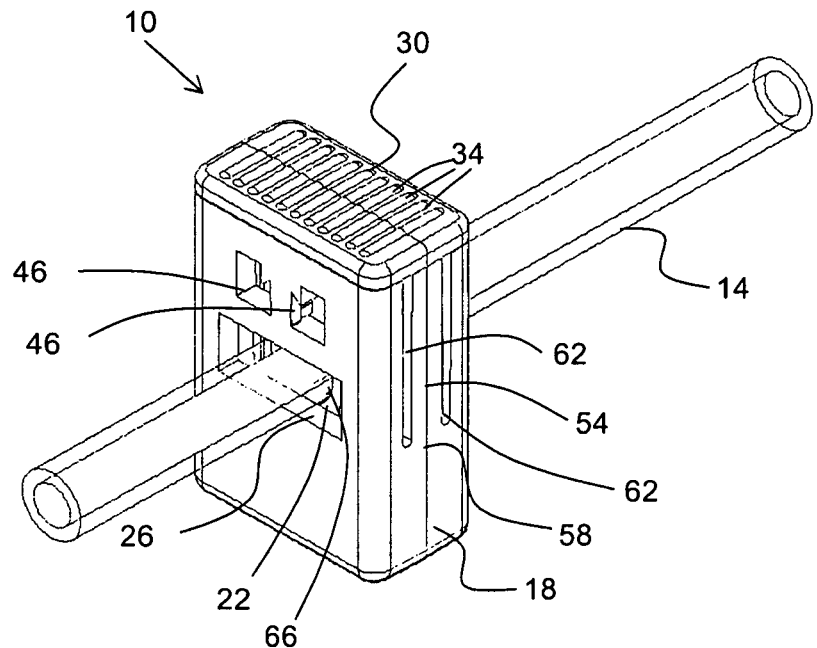
FIG. 2 shows another perspective view of the safety occluder and tubing portion shown in FIG. 1, with the occluder in second, open, non-occluding position.

Turning now to FIG. 2, there is shown a perspective view of the occluder 10 of FIG. 1. Rather than the plunger 22 being in the first, closed or occluding position, the handling portion 30 has been pushed down so that the opening 66 in the plunger is in alignment with the opening 26 in the body 18. This places the plunger 22 in a second, open or non-occluding position. In such an orientation, the plunger 22 and the body 18 no longer pinch closed the tubing 14. Thus, flow through the tubing 14 is allowed.

In common usage, the occluder plunger 22 is moved into the second, open or non-occluding position in one of two situations. If medical personnel want to prime the infusion tubing or otherwise want to allow solution to flow through the tubing 14, they may place a thumb or finger on the handling portion 30 and press down to move the plunger 22 into the position shown in FIG. 2.

If the occluder 10 is being placed in an infusion pump, the pump will typically have a door or other activating mechanism that will press and hold the plunger 22 so that the occluder is in second position while mounted in the pump. This allows fluid flow to be controlled by the pump uninterrupted by the occluder. If the door is opened or the occluder 10 is otherwise removed from the pump, a biasing member engaging the plunger 22 will move the plunger back into the first, closed or occluding position. Thus, the occluder 10 will not allow a free-flow situation to accidentally develop if the infusion set is removed from the pump.

Figure 3:
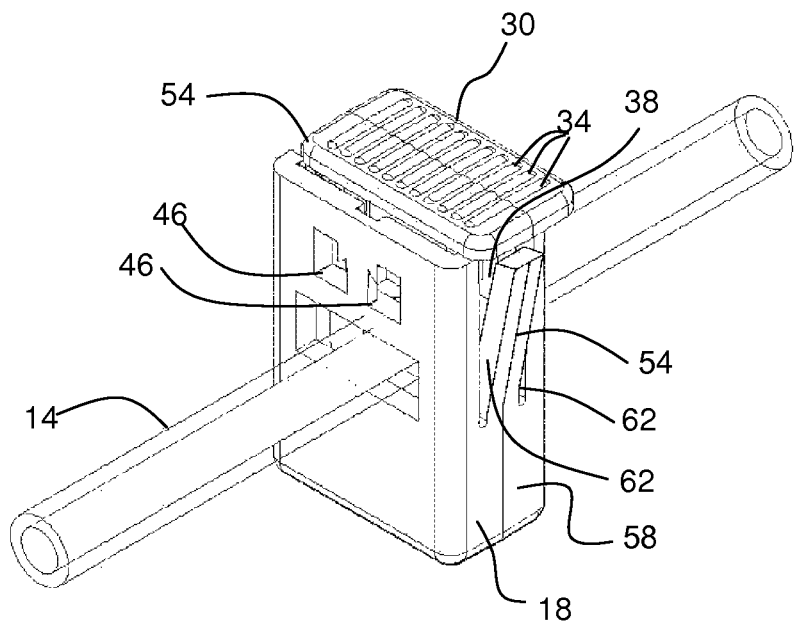
FIG. 3 shows another perspective view of the safety occluder and tubing portion shown in FIG. 1, with the occluder in a third, open, non-occluding position.

FIG. 3 shows a perspective view of the occluder 10 of FIG. 1 wherein the plunger 22 has been moved into a third, open or non-occluding position. This is accomplished by pivoting or moving the plunger 22 laterally to either side of the body 18 while the plunger is in the second, open or non-occluding position (FIG. 2) and allowing the plunger to rise slightly. As is shown below, this allows interaction between a projection and channels on the plunger 22 and the body 18 which prevents the plunger from returning to the first, closed or occluding position (FIG. 1). Thus, while the plunger 22 is in the third, open or non-occluding position, the occluder 10 is essentially locked open.

While it is often undesirable for free-flow to develop unchecked by an occluder or clamp or by a pump, there are times when a free-flow condition is needed. Such times may include an emergency situation in which multiple drugs are being delivered to the patient as quickly as possible. If the occluder is biased closed, a member of the medical staff must hold the occluder open to ensure fluid flow. This is distracting and lessens the availability of medical personnel to otherwise deal with the medical emergency. By sliding the handling portion 30 to either side and then releasing the plunger 22, the plunger is locked in an open orientation and free-flow through the infusion tubing 14 is assured.

It is thus seen that the plunger 22 moves laterally from the second, open or non-occluding position to a third, locked open and non-occluding position along a second path of movement. Thus, the occluder moves between a first, closed and occluding position and a second, open and non-occluding position along a first path of movement and the occluder moves between the second, open and non-occluding position and a third, locked open and non-occluding position along a second path of movement. The second path of movement is approximately perpendicular to the first path of movement.

FIG. 3 also shows the guides 54 formed by part of the sidewall 58 of the body 18. The guide 54 is deflected outwardly by the guide 38 of the plunger 22. If the handling portion 30 is depressed while the plunger is in the third, locked open and non-occluding position, the guide 54 will urge the plunger 22 back into the second, open and non-occluding position. Thereafter releasing the compressive force applied to the plunger will cause the plunger to return to the first, closed and occluding position (FIG. 1). Thus, the plunger 22 may be moved from the first, closed and occluding position to the second, open and non-occluding position and thereby to the third, locked open and non-occluding position by a user. The infusion tubing may then be primed and loaded into a pump configured to receive the occluder and hold the plunger 22 into the second, open and non-occluding position. When the occluder 10 is loaded into the pump, contact between the pump door and the plunger 22 will move the plunger downwardly relative to the body 18 and release the internal catch which holds the plunger 22 in the third position, allowing the guides 54 to move the plunger laterally into the second, open position. Thereafter, if the occluder 10 is removed from the pump the plunger 22 will move into the first, closed and occluding position.

Figure 4:
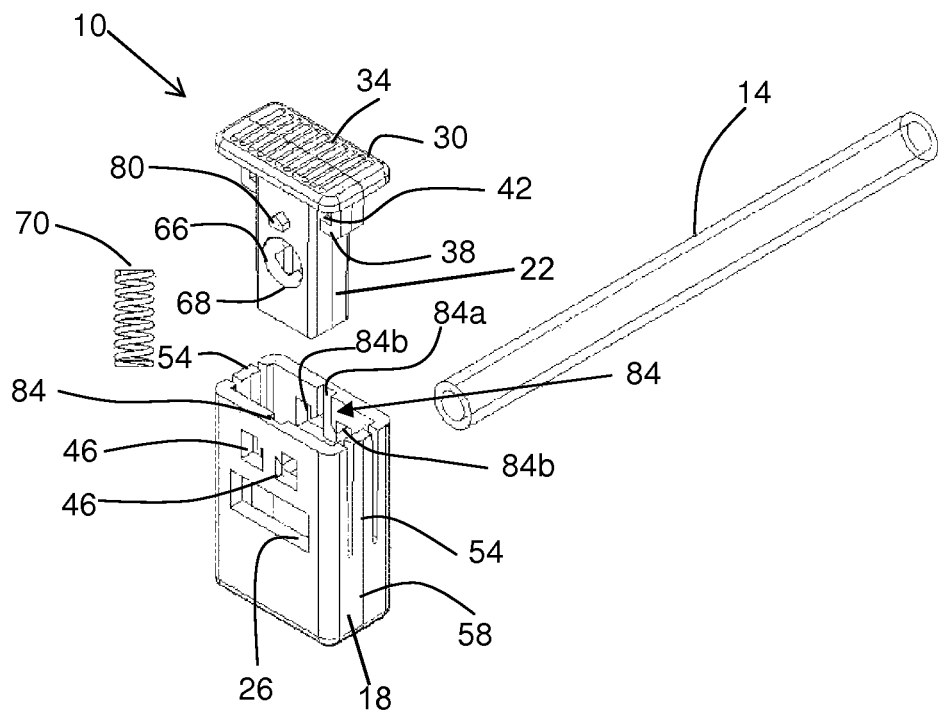
FIG. 4 shows an exploded view of the safety occluder and infusion set shown in FIG. 1.

Turning now to FIG. 4, there is shown an exploded view of the occluder 10 of FIG. 1 and infusion tubing 14. The occluder 10 is made up of three parts. The body 18, the plunger 22 and a biasing element 70, such as a spring. It will be appreciated that the biasing element 70 could be formed integrally with the plunger 22 or the body 18.

The exploded view shows several features of the invention in greater detail. For example, the plunger 22 includes an opening 66 through which the tubing 14 passes. When the plunger 22 moves upwardly, the bottom of the wall 68 defining the opening engages the bottom of the tubing 14, while the top wall defining the opening 26 on the body 18 engages the top of the tubing and pinches the tubing closed. When the openings 26 and 66 are in alignment, the tubing is able to pass through without being pinched closed. While opening 26 is shown as being rectangular and opening 66 is shown as being round, it will be appreciated that numerous different shaped openings could be used.

The plunger 22 also has one or more projections 80 which extend outwardly therefrom. The projection(s) 80 engage channels 84 in the body 18 to selectively control movement of the plunger 22. If the projection 80 is disposed in the center channel 84a, the plunger 22 will move generally vertically between the first, closed or occluding position and the second, open or non-occluding position. Pressing downwardly on the handling portion 30 opens the occluder 10 by moving the plunger 22 into the body 18 and releasing the handling portion similarly closes the occluder due to the biasing member 70. Thus, the plunger 22 moves vertically along the first path of movement as the projection 80 moves vertically in slot 84a.

To either side of the center channel 84a is a lateral or locking channel 84b, corresponding to the second path of movement. Having two lateral channels 84b on either side of the channel 84a allows the occluder to be locked in the third, open position by moving the plunger 22 to either side of the body 18. It is seen how the lateral channels 84b extend sideways for a distance and then have an upwardly extending portion. The biasing element 70 will keep the projection 80 locked in the upwardly extending portion of the lateral channel 84b once placed in this position. If the plunger 22 is pivoted or moved toward either lateral side and allowed to move upwardly, the projection 80 becomes retained in the lateral side or locking channel 84b. This holds the plunger in the third, locked open or non-occluding position and keeps the occluder there until force is applied to the handling portion 30 of the plunger 22. As the plunger 22 is pushed downwardly a sufficient distance, the projection 80 is moved out of the upwardly extending portion of the lateral channel 84b, and the guide 54 will push the plunger 22 back into the second, open or non-occluding position. If pressure is not maintained on the handling portion 30, the plunger 22 will then be forced into the first, closed or occluding position by the biasing element 70.

Turning now to FIGS. 5A, 5B and 5C, there are shown cross-sectional views of the occluder 10 of FIG. 1, including the plunger 22 and the body 18. The infusion set tubing 14 shown in FIGS. 1 through 4 has been omitted for clarity. It will be appreciated, however, that the tubing 14 would be positioned in the openings 26 and 66 in the body 18 and plunger 22, respectively.

In FIG. 5A, the plunger 22 is shown in the first, closed or occluding position which is shown in perspective in FIG. 1. The opening 66 in the plunger 22 is not in alignment with the opening 26 in the body 18. It will be appreciated that there are overlapping areas in which portions of the opening 66 align with portions of the opening 26. However, these areas are sufficiently small that they will be completely or nearly completely filled by the tubing 14 and the tubing is pinched closed. Thus, as used herein, a statement that the openings are not in alignment means that the openings are sufficiently out of alignment as to pinch and thereby occlude flow through the infusion set. Likewise, the openings 26 and 66 need not be in complete alignment, i.e. one opening may extend further in one direction than the other, without preventing or substantially preventing flow through the infusion tubing 14. Thus, a reference that the openings are in alignment means that the alignment is such that the tubing 14 is not pinched to the point of materially affecting flow through the infusion tubing.

FIG. 5E shows the position of the projection 80 in the center channel 84a when the plunger 22 is in the first, closed or occluding position. It will be noted that the projection 80 is provided with a beveled top and the channel 84a is provided with beveled side walls. The sloped walls on the projection 80 and the channel 84a interact to ensure that if the plunger 22 is released from the second, open or non-occluding position (FIG. 5B and 5F), the biasing element 70 will force the plunger back into the first, closed or occluding position. The plunger 22 (and projection 80) may move through the first path of movement by moving vertically in the slot 84a as shown by arrow 86a.

FIG. 5B shows the position of the plunger 22 when it is in the second, open or non-occluding position. The plunger 22 has been slid down in the body 18 so that the opening 66 of the plunger is in alignment with the opening 26 of the body—thereby not pinching closed the tubing 14. (The relative positions of the openings 26 and 66 will depend on their relative size and positioning). This is the position in which the plunger 22 will normally be in when the occluder is disposed in an infusion pump. A door or other similar structure will hold the plunger 22 and body 18 relative to one another so that flow is enabled through the tubing.

FIG. 5F shows the relative positions of the projection 80 and the channels 84a and 84b. While it is shown that the projection 80 extends from the plunger 22 and the channels 84 are formed into the body 18, it will be appreciated that the projection could be formed on the body and the channels formed on the plunger.

If pressure on the plunger 22 is released, the biasing element 70 will move the plunger upwardly and the projection 80 will follow the channel 84a to return the plunger to the first, closed or occluding position as indicated by arrow 86a. Thus, in normal usage, the plunger 22 follows a first path of movement when it is moved either from the application of a force, or a force in the opposite direction due to the biasing element 70.

Figure 5G:
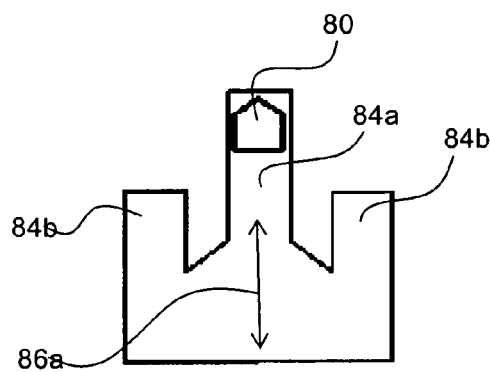
FIG. 5G shows a projection and channels from the plunger and body of the occluder when the plunger is in the third, open, non-occluding position.
Figure 5G:
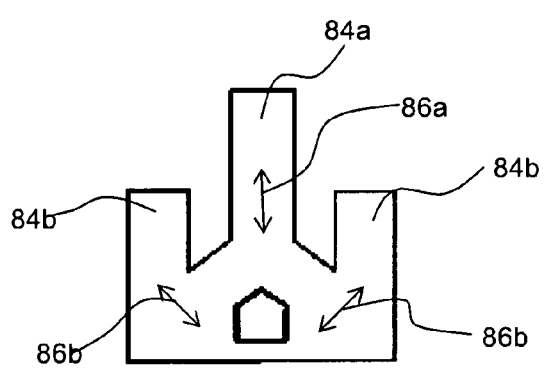
Figure 5G:
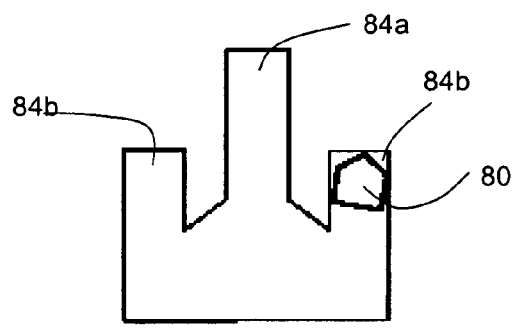

The plunger 22 can also move along a second path of movement. Instead of being moved vertically, the plunger can be pivoted or moved horizontally so that the plunger moves to either side before it rises under the force of the biasing element 70. This second path of movement, indicated by arrows 86b, causes the projection 80 to move into one of two side channels 84b. The side channels 84b extend upwardly to a lesser extent than the central channel 84a, and thus allow the projection 80 to be held captive therein but limit the distance the plunger 22 can travel such that the occluder 10 does not prevent flow through the tubing. Thus, the opening 66 in the plunger 22 is in general alignment with the opening 26 in the body 18 (i.e. the tubing 14 will not be pinched closed—although the alignment between the openings may change somewhat). In other words, the plunger 22 can be released and it stays in the third, open or non-occluding position as shown in FIGS. 5C and 5G. This is typically accomplished by a user pressing the plunger 22 into the second, open or non-occluding position, and then applying force to the handling portion 30 to slide the top of the plunger toward either side of the body and letting off slightly on the downward pressure. Once the projection 80 is in one of the side channels 84b, the plunger 22 is locked in the third, open or non-occluding position until a downward force is applied to the plunger and the guides 54 or the user re-center the plunger and projection.

When the plunger 22 is locked in the third, open or non-occluding position, the infusion set tubing is in free-flow mode and no additional effort is needed by medical personnel to keep it in that position. Thus, medical personnel have improved control over the function of the occluder 10.

It will be appreciated that once the emergency or other need for free-flow is over, the medical personnel need merely press down on the handling portion 30 and the plunger 22 will move back into the first, closed or occluding position. If the medical personnel forget to move the plunger out of the third position, reloading the occluder 10 in the pump can automatically do so, as is illustrated in FIG. 5D. When the pump door 98 closes, it will push downwardly on the plunger 22 and the guides 54 move the plunger back into the second position. If the pump door is reopened or the occluder 10 is otherwise withdrawn from the pump, the plunger 22 will automatically return to the first position and prevent free-flow through the tubing 14.

Figure 6:
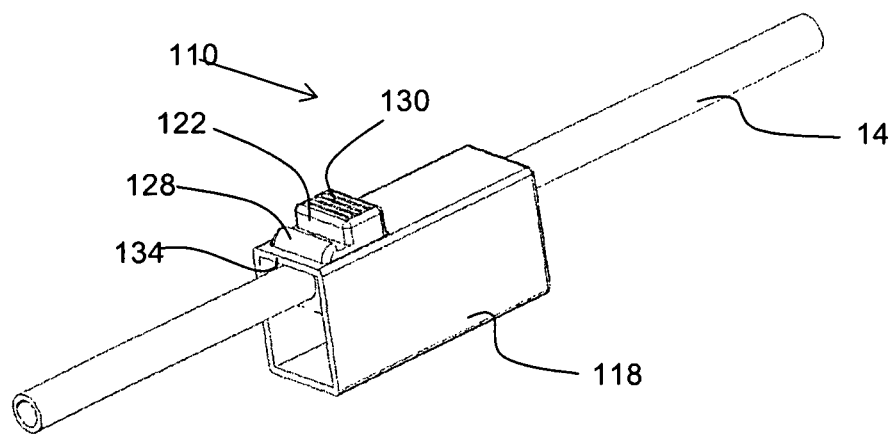
FIG. 6 shows a perspective view of an alternate configuration of a safety occluder and tubing of an infusion set in accordance with principles of the present invention.

Turning now to FIG. 6, there is shown an alternate configuration of the present invention. The occluder, generally indicated at 110, receives a tubing portion 14 of an infusion set to selectively occlude flow therethrough. The occluder 110 includes a body 118 and a plunger 122. As with the previous configuration, the plunger 122 is biased into a first, closed or occluding position wherein the plunger pinches closed the tubing 14 of the infusion set.

Also shown in FIG. 6 is an arm or projection 128 which extends from the plunger 122. When a handling portion 130 of the plunger 122 is pressed down into a second, open or non-occluding position, the plunger can be slid forwardly so that the projection 128 engages a holding wall 134 of the body 118, thus holding the plunger in a third, open or non-occluding position. With the projection 128 engaging the holding wall 134, the plunger 122 is held in the third position and is not able to return to the first position. In such an orientation, free-flow through the tubing 14 is allowed. Once free-flow is no longer desired, the handling portion 130 is depressed and the plunger 122 is allowed to move back into the second position. When the handling portion 130 is released, the plunger automatically returns to the first position—where it prevents fluid flow through the tubing 14 due to the biasing element discussed in additional detail below.

Figure 7:
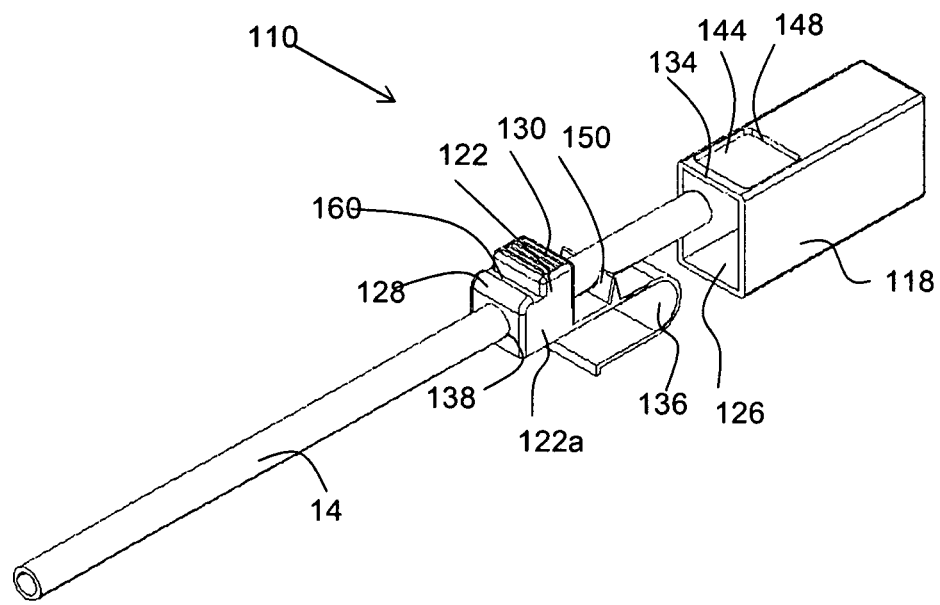
FIG. 7 shows an exploded view of the configuration of FIG. 6.

FIG. 7 shows an exploded view of the occluder 110 of FIG. 6. The body 118 includes a large channel 126 through which the tube 14 passes. The body 118 also holds a portion of the plunger 122 which has a biasing element 136 which is integrally formed as part of the plunger. The plunger 122 also includes a channel 138 which receives the tubing 14. Occluding the tubing can be performed in several ways depending on the orientation of the plunger 122 and the channel 126 in the body 118. For example, the plunger 122 may include a head portion 122a which defines the channel 138. If the head portion 122a extends upwardly through a hole 144 in the body 118, the tubing 14 will be pinched closed between the top wall 148 of the body (or a structure extending therefrom) and the bottom wall of the portion of head portion which defines the opening 138. Likewise, the tubing 14 can be pinched closed between the part of the head portion 122a defining the bottom of the opening and the holding wall 134.

In the alternative, the plunger 122 can include a pinching member 150 which is disposed along the plunger so as to pinch the tubing 14 closed against the top wall 148 of the body 118 when the plunger head portion 122a is extending upwardly through the hole 144, but not when the plunger head portion is moved into the second or third positions. Either way, the plunger 122 has a first, occluding position, a second, non-occluding position in which, if released, it will return to the first occluding position, and a third, non-occluding position in which it is temporarily locked into a configuration that will allow free flow.

If the occluder 122 is in the third, non-occluding position and the occluder is disposed in a pump with a door or other actuating mechanism, the occluder may be depressed so that it moves back into the second, non-occluding position, and ultimately back into the first, occluding position in the event that the door is opened or the infusion set is otherwise removed from the pump.

Figure 8A:
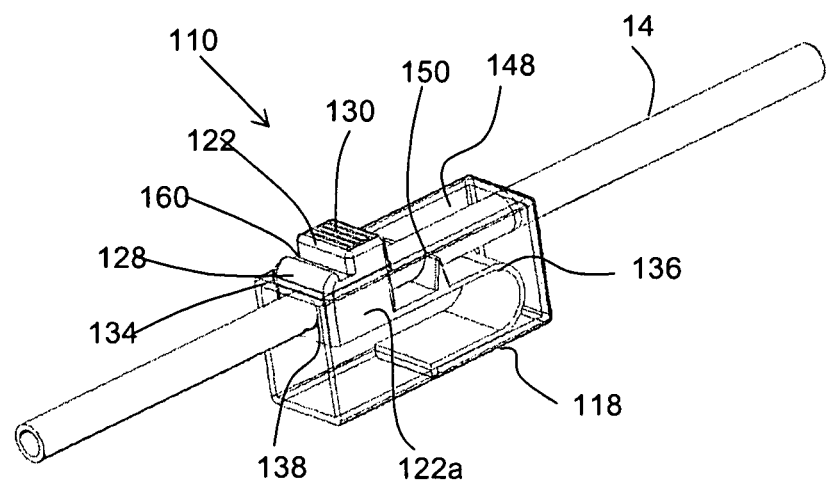
FIG. 8A shows an internal perspective view of the safety occluder of FIG. 6 when the plunger is in the first, closed, occluding position.

Turning now to FIG. 8A, there is shown an internal perspective view of the occluder 110 with the walls of the body 118 being transparent to show the inner workings. The plunger 122 is in a first, occluding position. The tubing 14 is pinched closed by the pinching member 150 which is disposed along the biasing element 136 of the plunger. The pinching member 150 forces the tubing 14 against the top wall 148 of the body and pinches the tubing closed to prevent flow through the tubing.

Figure 8B:
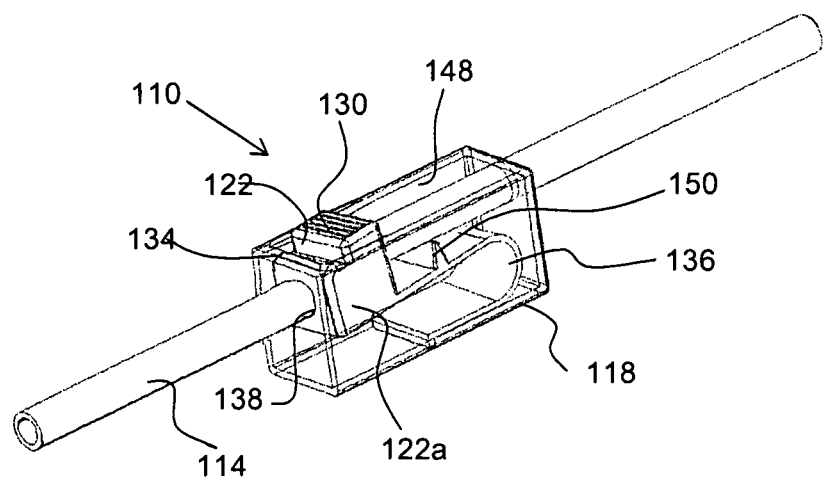
FIG. 8B shows an internal perspective view of the safety occluder of FIG. 6 when the plunger is in the second, open, non-occluding position.

FIG. 8B shows the plunger 122 being depressed into the second, non-occluding position. The application of force down on the handling portion 130 moves the plunger head 122a to move downwardly and forces the pinching member 150 to move away from the top wall 148 sufficiently that the tubing 14 is no longer occluded. If the force on the handling portion 130 is removed, the biasing element 136 will force the plunger head 122a upwardly, and will cause the pinching member 150 to again pinch the tubing 14 closed as it forces it against the top wall 148.

Figure 8C:
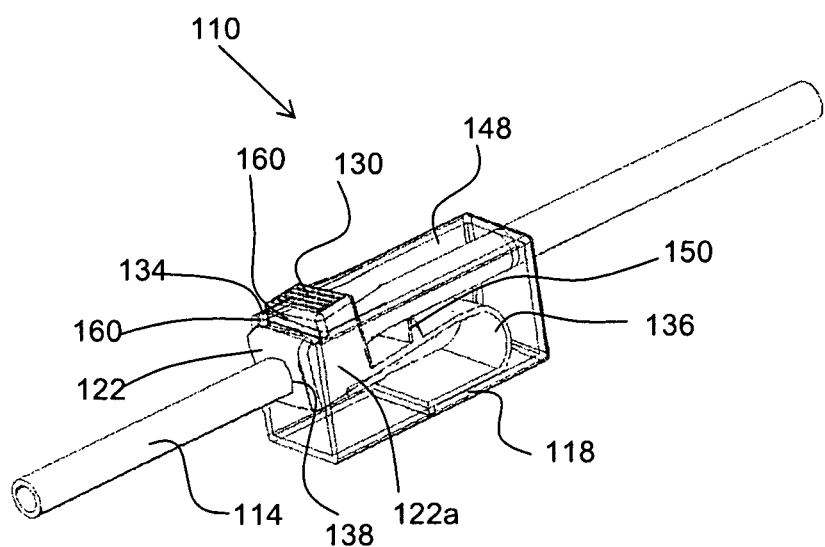
FIG. 8C shows an internal perspective view of the safety occluder of FIG. 6 when the plunger is in the third, open, occluding position.

FIG. 8C shows the plunger head 122a being depressed and push forwardly so that the projection 138 extends beyond the holding wall 134 and the holding wall fits into a groove or channel 160 (best seen in FIGS. 8 and 8A) between the projection and the handling portion 130. This holds the plunger head 122a in the position shown in FIG. 8C even if pressure is removed from the handling portion 130. This, in turn, holds the pinching member 150 away from the top wall 148 sufficiently that the pinching member and top wall no longer occlude the tubing. Thus, the occluder 110 is locked in an open position that allows free-flow through the infusion set. To remove the occluder 110 from the free-flow configuration, all that must be done is to apply a downward force on the plunger head 122a. This can be accomplished by medical personnel directly, or by insertion of the occluder 122 into an infusion pump, or the like, and actuating the door or other structure which is used to hold the occluder open. If the door, etc., is opened, the occluder 110 will return to the first, occluding position and prevent a free-flow situation from developing.

Figure 9:
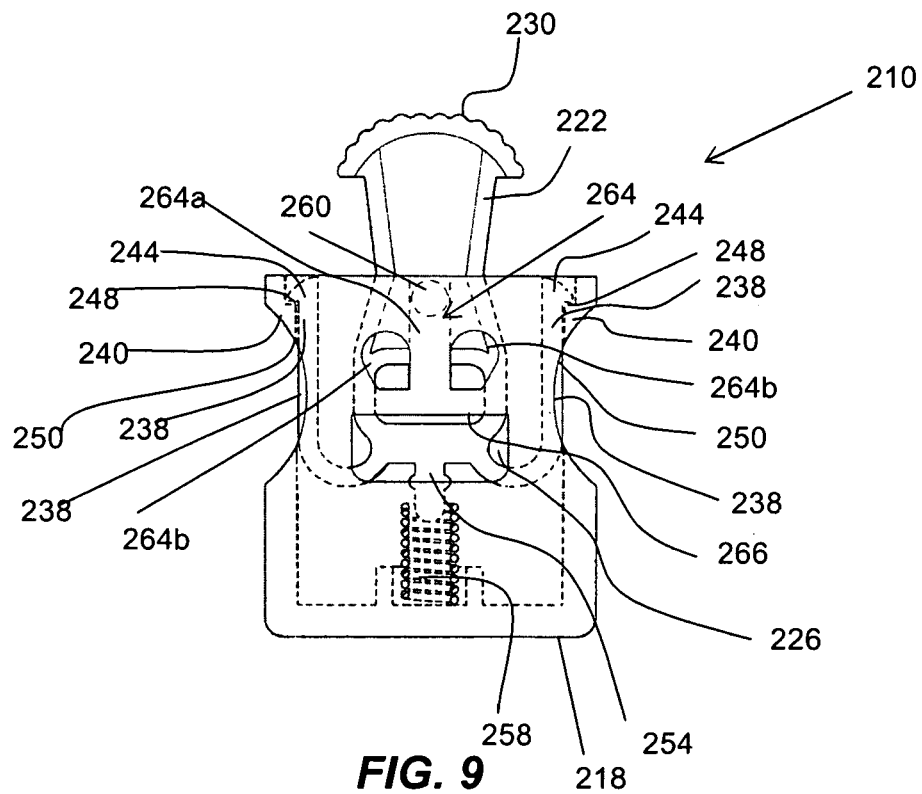
FIG. 9 shows a front view of an alternate configuration of a safety occluder having a locking mechanism for maintaining the occluder in a first, closed or occluder position.

Turning now to FIG. 9, there is shown a front view of yet another configuration of a safety occluder, generally indicated at 210. The occluder 210 includes a body 218 and a plunger 222 which slides in the body to selectively pinch closed a tube of an infusion set in a similar manner discussed above with references to the other configurations.

The occluder 210 shown in FIG. 9 is in a first, closed or occluding position in which the plunger 222 and the body 218 will cooperate to pinch closed the tubing of the infusion set which passes through the occluder 210. Thus, the body 218 has one or more openings 226 through which the infusion set tubing passes. The plunger 222 also includes an opening 266 for receiving a portion of the tubing. When the opening 226 of the body 218 and the opening 266 of the plunger are in alignment, the tubing is not pinched off and fluid can flow through the tubing. When the two openings 226 and 266 are out of alignment—as shown in FIG. 9, tubing extending through the openings is pinched closed.

Similar to the prior configurations, the plunger 222 includes a handling portion 230 disposed at the top thereof. The handling portion 230 includes a plurality of grooves, protrusions or other tactile features 234 to provide the user with a gripping surface on the plunger. As will be explained in additional detail below, the handling portion 230 is used to pull the plunger 222 out of its normal path of travel between the first, closed or occluding position shown in FIG. 1 and a second, open or non-occluding position.

The plunger 222 also includes a pair of guides 238 which help center the plunger in the body 218. The guides 238 are formed as elongated, curved arms and engage the walls 240 of the body 218. The guides 238 act in a somewhat similar manner to the guides 54 in the body 18 in FIG. 1, etc., in that they can be deflected out of their ordinary position and then return to their original position so center the plunger if needed.

The guides 238 also serve another important purpose. The guides 238 interact with walls 240 of the body to limit movement of the plunger 222. More specifically, each of the guides 238 includes a catch 244. The catches 244 engage a ledge 248 along the walls 240 and prevent the plunger 222 from being moved from the first, closed or occluding position. In order to move the plunger 222, the guides 238 must be moved inwardly so that the catches 244 no longer engage the ledges 248 of the wall sufficiently to stop movement of the plunger toward the opening 226. To facilitate this movement of the plunger 222, a pair of openings 250 are formed in the body 218 to expose a portion of the guides 238. If the user presses inwardly on the guides 238, the catches 244 are moved inwardly and the plunger 222 can be moved from the first, closed or occluding position into a second, open or non-occluding position.

The bottom of the plunger 222 has a mount 254 which engages a spring 258 or other biasing member. The spring 258 or other biasing member is configured to bias the plunger 222 back into the first, closed or occluding position. Thus, if a user presses inwardly on the guides 238 and presses downwardly on the handling portion 230, the plunger 222 will move into the second, open or non-occluding position in which fluid can flow through the tubing. As soon as pressure is removed from the handling portion 230, however, the spring 258 will push the plunger 222 back into the first, closed or occluding position. Thus, the occluder 210 cannot be accidentally opened by, for example, a person rolling over onto the occluder, and cannot be accidentally left open.

The occluder 210 can, however, be intentionally left open in a situation where the medical personnel desire a free flow condition. As with the configurations shown and discussed above, a projection 260 and grooves or channels 264 are used to allow the plunger 222 to be selectively locked open. This is accomplished in the configuration shown in FIG. 9 by pressing down on the plunger 222 while pressing inwardly on the guides 238 to overcome the locking mechanism. Once the plunger 222 is moved down into the second, open or non-occluding position, the user would push the handling portion 230 to either side so that the projection 260 would nest in one of the channels 264b. The channels 264b are configured to limit the upward movement of the projection and thus the plunger 222. The channels 264b are also configured to prevent lateral movement of the projection near the end thereof so that the guides 238 cannot return the plunger to a centered position without again pressing down on the plunger 222.

Once the plunger 222 is pressed down sufficiently that the channels 264b no longer prevent lateral movement of the projection 260, the guides 238 will center the plunger and the spring 258 will force the plunger back into the first, closed or occluding position. Thus, the occluder 210 provides a locking mechanism which prevents movement of the plunger 222 out of the first, closed or occluding position, and another locking mechanism which prevents the occluder from being moved out of the third, open or non-occluding position, thereby providing a locked closed and a locked open configuration.

Figure 9A:
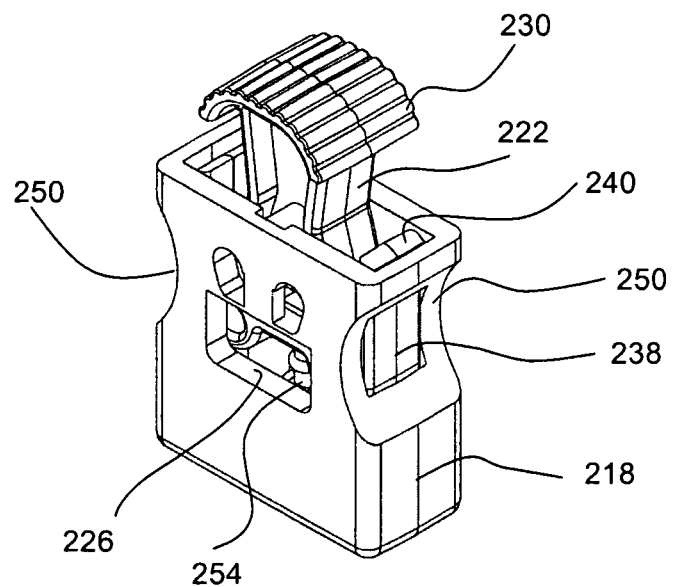
FIG. 9A shows a perspective view of the safety occluder of FIG. 9.
Figure 9B:
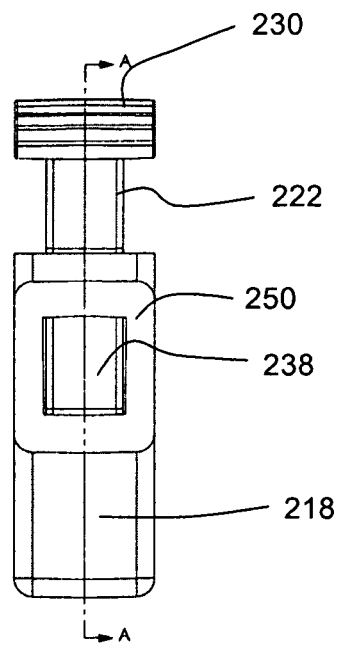
FIG. 9B shows a side view of the safety occluder of FIGS. 9 and 9A.
Figure 9C:
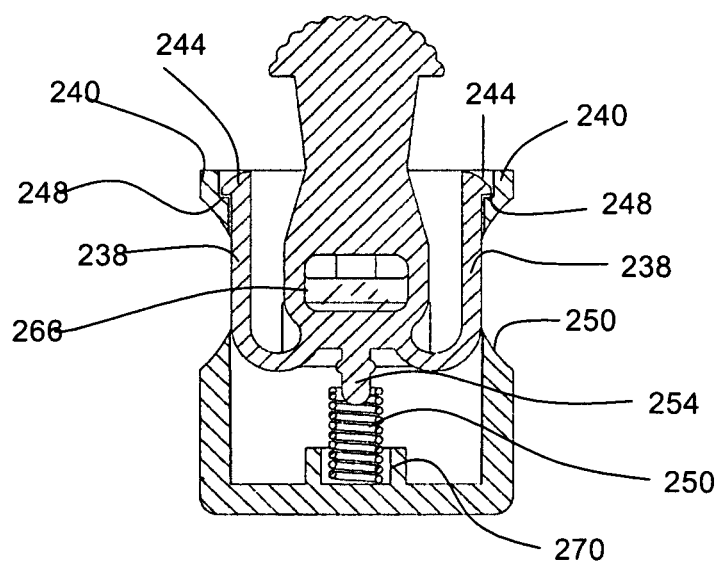
FIG. 9C shows a cross-sectional view of the occluder of FIGS. 9 through 9B taken along line A-A in FIG. 9B.

FIGS. 9A, 9B and 9C show a perspective view, a side view and a cross-sectional view of the safety occluder 210. The cross-sectional view in FIG. 9C shows the internal elements shown in shadow in FIG. 9 and also shows a mounting structure 270 for holding the bottom of the spring 258.

It will be appreciated that the occluder 210 can be made to be very small and compact, while at the same time providing improved functionality over many of the prior art occluders. The two handed operation (or very dexterous one handed operation) is advantageous because it prevents accidental openings of the valve as may occur if a patient were to roll over on the occluder 210, or the occluder were to become jammed between hospital equipment or between the patient's bed and the wall. Once the initial locking mechanism created by the guides 238 and walls 240 is overcome, the plunger 222 can be moved into the second, open or non-occluding position, or into the third, open or non-occluding position by simply manipulating the handling portion 230 with the user's thumb. Likewise, the locking mechanism which holds the plunger 222 in the third, open or non-occluding position can be overcome by simply pressing down on the plunger with the user's thumb. Likewise, placing the occluder 210 in a pump and closing the door will push the plunger 222 back into the second, open or non-occluding position, where it can return to the first, closed or occluding position if the door is opened or the occluder 210 is otherwise removed from the pump.

Turning to FIG. 10A, there is shown a perspective view of an occluder, generally indicated at 310, disposed along a piece of tubing 14 of an infusion set. Only a small section of the tubing has been shown in the drawing for clarity. However, it will be appreciated that the tubing 14 will typically be connected to a solution reservoir at one end, and to an infusion adapter at an opposing end. The infusion adaptor may be an adaptor for connection to a stoma tube in the context of enteral feeding or an IV needle in the context of parenteral solutions.

The occluder 310 shown in FIG. 10A is disposed in a first, closed or occluding position. The occluder 310 includes a body 318 and a plunger 322. The body 318 includes a void into which the plunger 318 is slidably positioned. The body 318 includes openings 326 on each side to receive the tubing 14 of the infusion set. The plunger 322 also includes an opening for receiving a portion of the tubing.

When the opening in the plunger 322 is not in alignment with the openings 326 in the body, the sidewall defining the opening in the plunger and an opposing sidewall defining the opening in the body will pinch closed the tubing 14 and prevent fluid to flow therethrough in a manner similar to that discussed above. The amount of overlap between the openings which may be present while still having the openings be "out of alignment" will depend on the diameter of the tubing and the thickness of the tubing when it is pinched closed.

As shown in FIG. 10A, the plunger 322 includes a handling portion 330 disposed at the top thereof. The handling portion 330 includes a plurality of grooves, protrusions or other tactile features 334 to provide the user with a grip on the plunger. As will be explained in additional detail below, the handling portion 330 is used to rotate the plunger 322 which will, due to intervening structure, prevent movement of the plunger along its normal path of travel between the first, closed or occluding position shown in FIG. 10A and a second, open or non-occluding position.

Also shown in FIG. 10A is a channel 364 extending from at or near the top of the body 318. The channel 364 intersects with a channel 364b disposed lower on the body. A projection (not shown in FIG. 10A) slides in the channel 364 when the plunger 322 is moved from a first, closed or occluding position, shown in FIG. 10A into a second, open or non-occluding position. As will be discussed in additional detail below, the plunger can also be rotated as the projection moves into channel 364b. The channels 364 and 364b form a generally J-shaped channel. As long as the projection is in the vertical portion of the J-shaped channel, it will return to the first, closed or occluding position. However, if the plunger 322 is pushed down into the second, open or non-occluding position and rotated, the projection will move into the tail of the J-shaped channel and will be held therein. Thus, the plunger 322 remains held in a third, open or non-occluding position, allowing free flow through the tubing 14.

FIG. 10B shows a side view of the safety occluder 310 in a first, closed or occluding position wherein the plunger 322 and the body 318 interact to pinch closed the tubing 14. Also visible is the channel 364b (channel 364 being shown in shadow) and a biasing element 370, such as a spring.

Figure 10C:
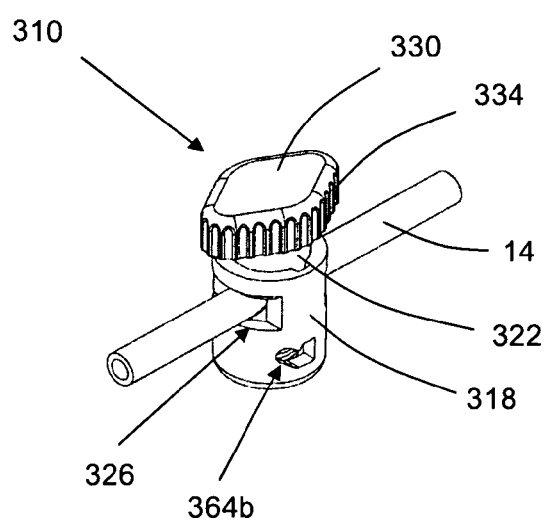
FIG. 10C shows a side view of the tubing and safety occluder of FIG. 10 in third, open or non-occluding position so that the occluder is locked open.
Figure 10C:
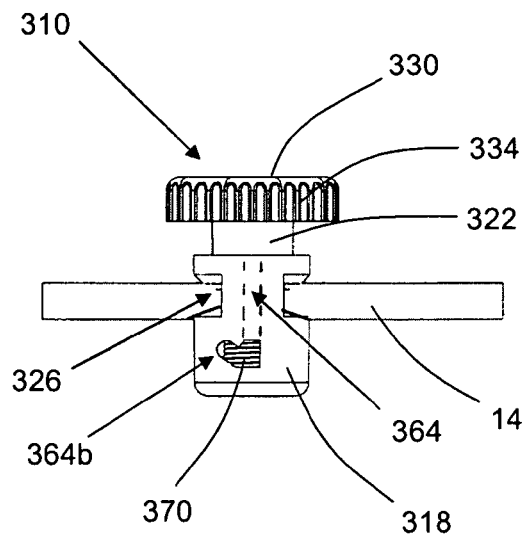
Figure 10C:
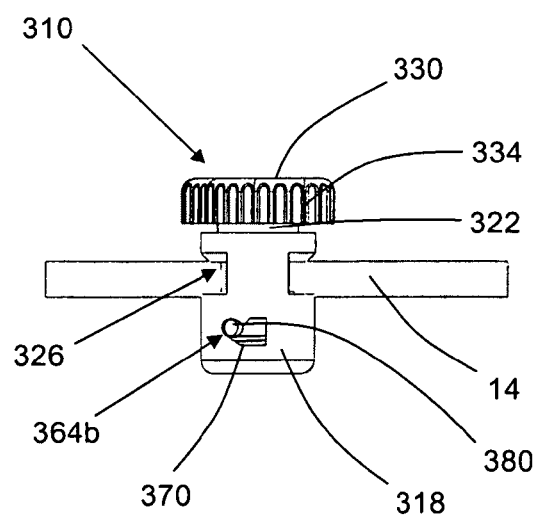

FIG. 10C shows a side view of the occluder 310 wherein the plunger 322 has been moved into the third, open or non-occluding position. The handling portion 330 has been used to push downwardly on the plunger 322 against the biasing element 370, and then the occluder is given a small rotation to move the projection 380 into the channel 364b where the projection prevents the plunger 322 from returning to the first, closed or occluding position. Thus, the occluder 310 is held in an open configuration, thereby allowing free flow through the tubing 14 of the infusion set.

Figure 10D:
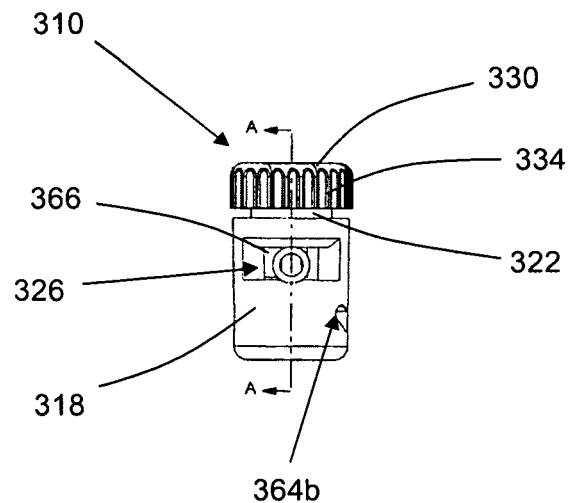
FIG. 10D shows an end view of the tubing and safety occluder of FIG. 10C.
Figure 10E:
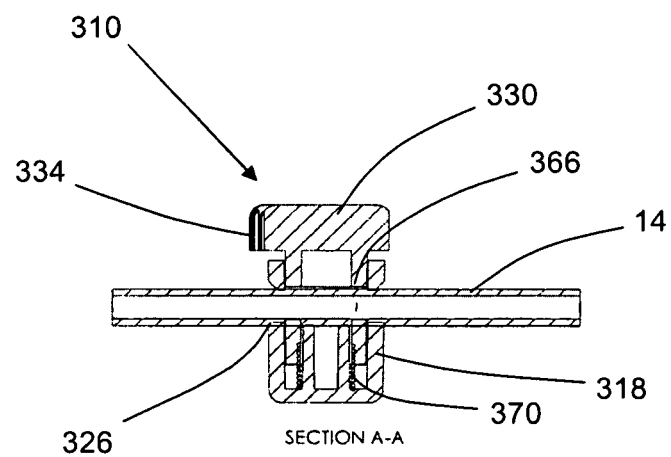
FIG. 10E shows a cross-sectional view taken along line A-A in FIG. 10D with the safety occluder locked open.

FIGS. 10D and 10E show, respectively, an end view and a side cross-sectional view of the occluder 310 locked in the third, open or non-occluding position. In this position, the projection 380 and channel 364b interact to keep the opening 366 in the plunger 326 in sufficient alignment with the openings 326 in the body 318 that flow is permitted through the tubing. Pressing down on the plunger 326 moves the projection 380 in the channel 364b and returns the plunger 322 to the second, open or non-occluding position. As soon as pressure is released from the plunger 322, the biasing element 370 will return the plunger to the first, closed or occluding position.

Figure 11A:
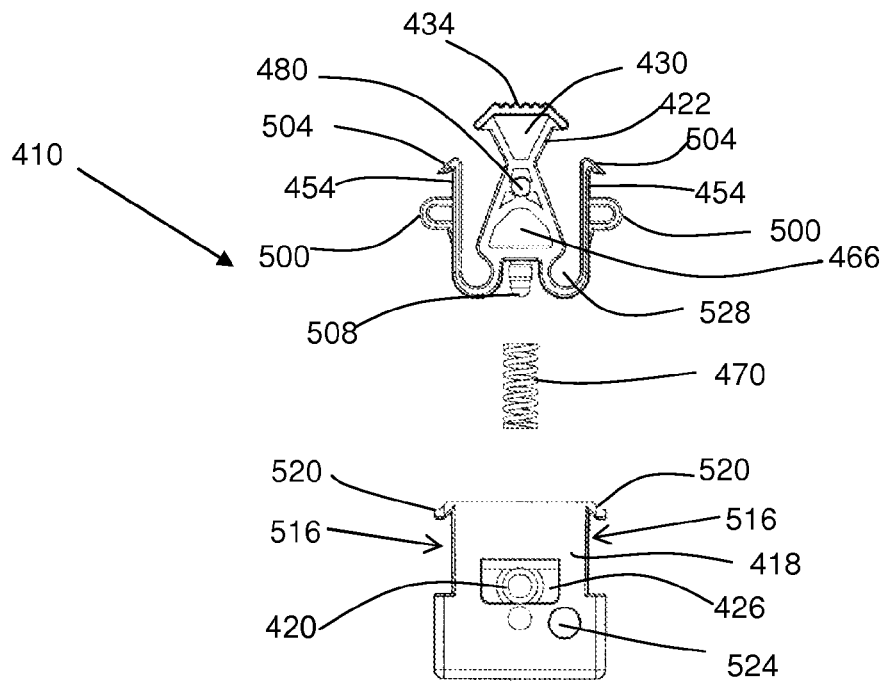
FIGS. 11A through 11D show another embodiment of a safety occluder of the present invention.
Figure 11B:
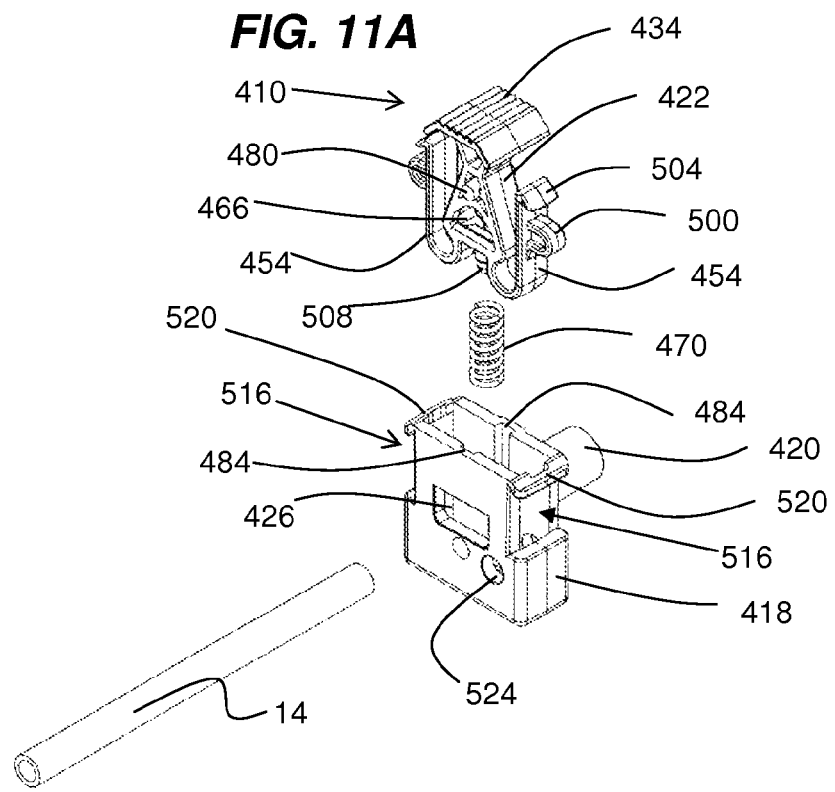

Turning now to FIGS. 11A through 11F, another occluder of the present invention is shown. The occluder is optimized for use with a pump. FIGS. 11A and 11B show exploded views of the occluder 410 and a section of tubing 14. The occluder 410 includes a body 418, plunger 422 and spring 470. The occluder 410 functions in a manner similar to that of the occluder 10 of FIGS. 1 through 5 and the occluder 210 of FIG. 9 and the descriptions thereof similarly apply to the occluder 410. The tubing 14 passes through openings 426 in the front and back of the body 418 and an opening 466 in the plunger 422. The plunger includes a handling portion 430 with grooves 434 formed therein to allow the occluder 410 to be actuated manually or with a pump door. The body 418 includes a coupler section 420 which is used to join a soft pumping tubing with a less expensive tubing which forms the majority of the infusion tubing. It will be appreciated that the coupler 420 may be omitted and the occluder used with a continuous section of tubing. The plunger includes a post 508 which, along with a recess 512 formed in the body 418, locates the spring 470. The occluder 410 also includes a hole 524 in the body 418 which allows a shipping pin to be inserted through the hole 524 and the opening 528 formed by a guide arm 454 to lock the occluder in an open, non-occluding position. While not typically used during normal operation of the occluder 410, the hole 524 and opening 528 allow the occluder 410 to be locked open for shipping to prevent damage to the soft pumping tubing 14. Release of the shipping pin will cause the occluder 410 to automatically move to the first, closed and occluding position.

The plunger 422 includes pins 480 which interact with channels 484 in the body 418 to keep the plunger properly located in the body. Although the channels 484 are not formed with lateral channels 484b as shown in FIGS. 1 through 5 and 9, the occluder 410 may be so formed so as to allow the occluder to be locked open in a third position as discussed previously. The plunger 422 includes guides 454 extending from the sides thereof. The guide arms 454 have release projections 500 and catch arms 504 extending therefrom. The release projections 500 extend through openings 516 in the sides of the body 418. The catch arms 504 interact with the openings 516 and the shoulder 520 of the body. The catch arms 504 lock the occluder 410 in the first, closed and occluding state unless the release projections 500 are pressed inwardly, bending the guides 454 and moving the catch arms 504 to a position where they do not engage the shoulders 520 of the body, allowing the plunger 422 to be pressed into the body 418 to allow flow through the tubing 14.

Figure 11C:
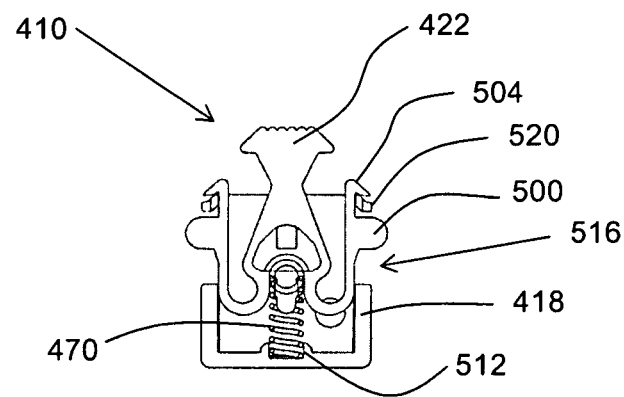
Figure 11D:
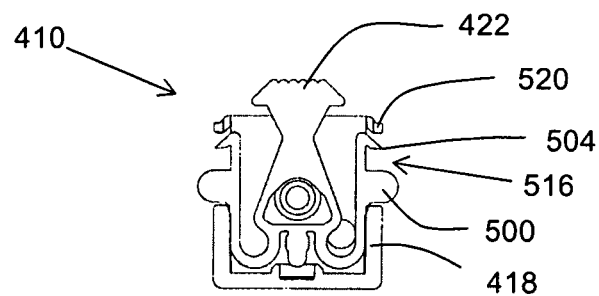

FIGS. 11C and 11D show cut-away views of the occluder 410. FIG. 11C shows the occluder in the first, closed and occluding position and FIG. 11D shows the occluder in the second, open and non-occluding position. For clarity, not all structures are shown or labeled although present in the occluder 410. FIG. 11C shows how the occluder, when in the first, closed and occluding position, is locked into the position by the catch arms 504 and the shoulders or ledges 520. The occluder 410 cannot be moved into the second, open and non-occluding position until the release projections 500 are pressed inwardly and the plunger 422 is simultaneously pressed downwardly relative to the body 418. This minimizes the risk of accidentally opening the occluder 410. If force is not applied to the plunger 422, the spring 470 (not shown in FIG. 11D for clarity) will press the plunger upwardly. The sloped upper surface of the catch arms 504 and the sloped lower surfaces of the shoulders 520 will cause the occluder to automatically move back to the first, closed and occluding position.

Figure 11E:
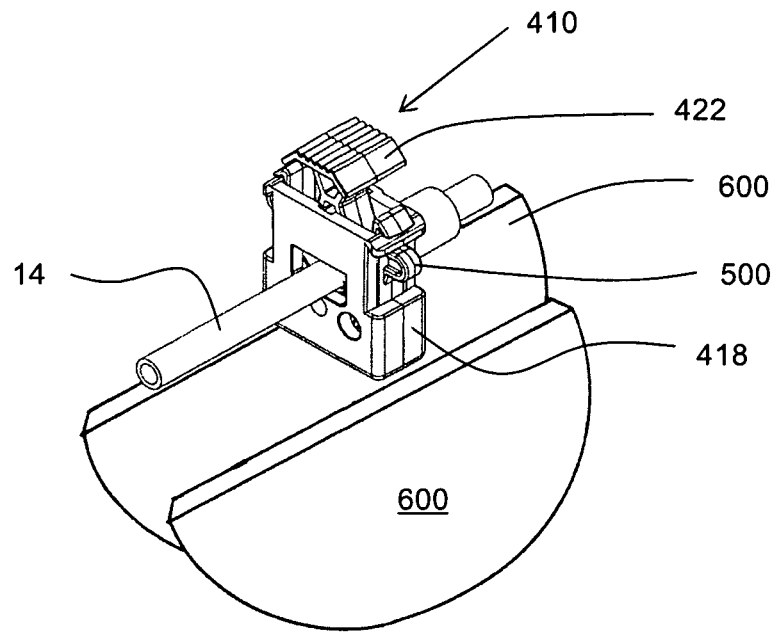
FIGS. 11E and 11F show the occluder of FIGS. 11A through 11D with an infusion pump of the present invention.

FIG. 11E shows the occluder 410 positioned adjacent the walls 600 of a pump, such as an infusion pump or feeding pump. The walls 600 of the pump form a channel into which the occluder 410 is placed and through which the tubing 14 is placed. The walls 600 guide the tubing around the pump mechanism. In loading the pump, the tubing is placed around the pump mechanism and the occluder 410 and tubing 14 are placed between the walls 600. The pump walls 600 are spaced apart to a distance approximately equal to the width of the occluder body 418. As a result, when the occluder 410 is placed between the walls 600, the walls press the release projections 500 inwardly and allow the plunger 422 to be depressed to allow flow through the occluder.

Figure 11F:
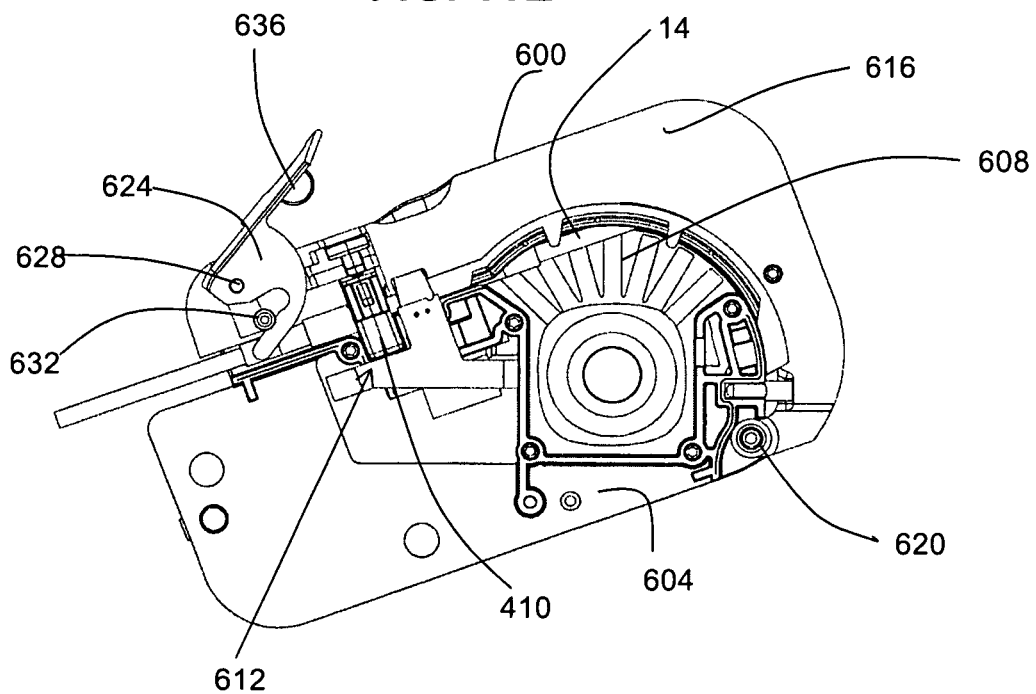

FIG. 11F shows the pump 604. The front wall 600 of the pump 604 has been removed to allow the internal parts of the pump to be shown. The rear wall 600 is largely blocked by other pump parts. The tube 14 is wrapped around the pump mechanism 608 (typically including actuating fingers and a cam type lobe similar to a linear peristaltic pump) and the occluder 410 is placed in a recess 612 in the pump 604. Since the width of the recess 612 and the distance between the pump walls 600 are only slightly more than the width of the occluder body 418, the release projections 500 are pressed inwardly to allow actuation of the plunger 422 when the occluder 410 is pressed into the recess 612.

A pump door 616 is mounted to the pump 604 at pivot 620, and extends around the side and top of the pump to hold the tubing 14 and occluder 410 mounted in the pump. The pump door 616 does not contact the plunger 422. The pump door latch 624 pivots around pivot 628 and engages latch 632 to hold the pump door 616 closed. The pump door latch 624 includes a projection 636 which engages the plunger 422 when the pump door latch is moved to secure the pump door closed. The pump door latch 624 cannot be closed until the pump door 616 is completely closed. Thus, the occluder is moved into the second, open and non-occluding position only after the pump door 616 is completely closed and secured shut with the pump door latch 624. As soon as the pump door latch 624 is opened, the plunger 422 is moved by the spring 470 and the occluder 410 moves into the first, closed and occluding position to prevent undesired flow through the tubing 14. The occluder thus provides an added measure of safety over previous pump-mounted occluders as it requires the pump door 616 to be properly closed and latched in place and the occluder 410 is actuated by properly closing the pump door latch 624 and not by the door alone. The closing of the pump door 616 ensures that the pumping fingers of the rotary peristaltic pump engage the tubing 14 and prevent free flow through the tubing before the occluder 410 is moved into the second, non-occluding position, providing an additional measure of safety against undesired free flow through the tubing.

Regardless of which configuration is used, a safety occluder is provided which is relatively simple and easy to use. The risk of accidental free-flow conditions are significantly reduced while allowing medical personnel to develop a free-flow condition when necessary. Additionally, the risk that the pump will not be able to close properly when the occluder is in the third, locked open position can be eliminated, as is the risk that the occluder will remain in the locked open condition if it is inadvertently removed from a pump, or if it is mounted in the pump while still locked open because the occluder will automatically move from the third, locked open and non-occluding position to the second, open and non-occluding.

While the discussion above has been principally in the context of an occluder which could be used to control the administration of fluids to a patient, it will be understood that the occluder could be used in a variety of non-medical applications. For example, the occluder could be used as a valve on resilient line to selectively allow flow. This may be particularly advantageous in a situation, where small quantities of liquid are usually dispensed, but occasionally larger amounts are needed. The occluder will dispense small amounts by simply pressing on the plunger. This will provide more accurate dispensing that a traditional faucet. However, when greater volumes are needed, the occluder can be locked into an open position to relieve the user of having to hold the occluder open for a prolonged period of time.

There is thus disclosed an improved safety occluder and method of use. It will be appreciated that numerous changes may be made to the present invention without departing from the scope of the claims. The appended claims are intended to cover such modifications.

What is claimed is:

1. An occluder for selectively preventing flow through tubing of an infusion set comprising:
   a body having an opening formed therethrough for receiving a tube and a space therein for receiving a plunger, the body comprising a ledge;
   a plunger movable within the space in the body, the plunger having an opening therethrough for receiving the tube, the plunger being movable in a first direction perpendicular to a tube passing therethrough between a first position wherein the occluder prevents flow through the tube and a second position wherein the occluder allows flow through the tube;
   a tube passing through the opening of the body while the plunger is in the first position and the second position; and
   a guide arm extending from the plunger, the guide arm having a catch formed thereon for engaging the ledge formed on the body to selectively prevent movement of the plunger from the first position to the second position;
   wherein the guide arm has a release projection disposed thereon, and wherein moving the release projection laterally inwardly moves the catch away from the ledge and allows the plunger to move to the second position.

2. The occluder according to claim 1, wherein the guide arm extends generally parallel to the first direction of movement.

3. A system comprising the occluder according to claim 1, and further comprising an infusion pump, and wherein the occluder is placed into a channel in the infusion pump, and wherein the channel is formed with a width such that placement of the occluder into the channel moves the release projection inwardly towards the body of the occluder and thereby allows movement of the plunger from the first position to the second position.

4. The system according to claim 3, wherein the pump comprises a pumping mechanism, a pump door and a pump door latch, and wherein closing the pump door presses the tube against the pumping mechanism and closing the pump door latch secures the door in a closed position, and wherein closing the pump door latch presses on the plunger to thereby allow flow through the tube.

5. The occluder according to claim 1, further comprising a second guide arm wherein the plunger has such that a pair of guide arms, including the guide arm and the second guide arm, is formed on opposing side of the plunger such that a pair of guide arms, including the guide arm and the second guide arm, is formed on opposing sides of the plunger.

6. An occluder for selectively inhibiting flow through a tubing, the occluder comprising:
   a body having an opening therethrough for receiving a portion of the tubing; and
   a plunger, the plunger having an opening therein for receiving a portion of the tubing, the plunger engaging the body and being slidable relative thereto such that the plunger and body pinch the tubing to inhibit flow therethrough when the opening of the body and the opening of the plunger are not in alignment, the plunger comprising a guide for selectively limiting movement of the plunger relative to the body;
   wherein the guide extends from plunger and a first position therein the guide prevents movement of the plunger relative to the body and a second position wherein the guide allows movement of the plunger relative to the body;
   wherein the guide has a projection for engaging the body to limit movement of the plunger;
   wherein the projection comprises a catch member extending from the guide for engaging the body and thereby preventing movement of the plunger, and wherein the guide is bendable to allow the catch member to disengage the body sufficiently to enable movement of the plunger relative to the body; and
   wherein the body comprises a ledge at one end thereof and wherein the catch member engages the ledge and prevents movement of the plunger to thereby prevent alignment of the opening in the plunger and the opening in the body unless the catch member is moved to enable the catch member to pass the ledge thereby selectively preventing movement of the plunger from the first position to the second position.

7. The occluder of claim 6, wherein the catch member is disposed in overlapping contact with the ledge and wherein the guide further comprises a projection extending away from the body, and wherein pressing inwardly on the projection moves the catch member to thereby allow the catch member to move beyond the ledge.

8. The occluder of claim 7, wherein the catch member comprises a catch arm disposed at the top of the guide.

9. The occluder of claim 8, wherein the body has a void with the plunger disposed therein, and wherein the guide comprises a projection extending into an opening in the body such that pressing on the projection moves the guide away from the inner wall of the body, and thereby moves the catch arm away from the ledge.

10. The occluder of claim 6, wherein the body comprises a void, and wherein the plunger moves generally linearly within the void from a first, closed and occluding position wherein the opening in the plunger is out of alignment with the opening in the body into a second, open and non-occluding position wherein the opening in the plunger is substantially in alignment with the opening in the body, and wherein the plunger comprises two guides extending from the plunger into engagement with the body to limit movement of the plunger from the first position into the second position.

11. The occluder of claim 10, wherein the guides comprise catch members which engage the body to selectively prevent movement of the plunger from the first, closed and occluding position to the second, open and non-occluding position.

12. The occluder of claim 11, wherein deflecting the guides enables the catch members to disengage the body sufficiently for the plunger to be moved into the second, open and non-occluding position.

13. The occluder of claim 12, wherein the occluder further comprises a biasing member disposed between the plunger and the body to automatically return the plunger to the first, closed and occluding position unless external force is applied to the plunger.

14. The occluder of claim 13, wherein the body comprises openings and the guides have projections extending into the openings such that pressing inwardly on the projections bends the guides inwardly and enables the catch members to disengage the body sufficiently to move the plunger into the second, open and non-occluding position.

15. The occluder of claim 14, wherein the catch members are disposed in the openings in the body which receive the projections when the plunger is disposed in the second, open and non-occluding position, and wherein the catch members are sloped to enable the catch members to deflect and return the plunger to the first, closed and occluding position when no external force is applied to the plunger.

16. A pump system, comprising:
an occluder for selectively inhibiting flow through a tubing, the occluder comprising:
a body having an opening therethrough for receiving a portion of the tubing; and
a plunger, the plunger having an opening therein for receiving a portion of the tubing, the plunger engaging the body and being slidable relative thereto such that the plunger and body pinch the tubing to inhibit flow therethrough when the opening of the body and the opening of the plunger are not in alignment, the plunger comprising a guide for selectively limiting movement of the plunger relative to the body;
wherein the body comprises a void, and wherein the plunger moves generally linearly within the void from a first, closed and occluding position wherein the opening in the plunger is out of alignment with the opening in the body into a second, open and non-occluding position wherein the opening in the plunger is substantially in alignment with the opening in the body, and wherein the plunger comprises two guides extending from the plunger into engagement with the body to limit movement of the plunger from the first position into the second position;
wherein the guides comprise catch members which engage the body to selectively prevent movement of the plunger from the first, closed and occluding position to the second, open and non-occluding position;
wherein deflecting the guides enables the catch members to disengage the body sufficiently for the plunger to be moved into the second, open and non-occluding position; and
wherein the occluder further comprises a biasing member disposed between the plunger and the body to automatically return the plunger to the first, closed and occluding position unless external force is applied to the plunger;
a pump comprising a housing having walls spaced apart to deflect the projections inwardly when the body of the occluder is slid between the walls.

17. The pump system of claim 16, wherein the pump further comprises a door and door latch disposed such that closing the door latch engages the plunger and moves the plunger from the first, closed and occluding position to the second, open and non-occluding position.

18. The pump system of claim 16, wherein the walls of the pump are generally parallel.

19. A fluid delivery set comprising:
a tubing
a body and a plunger slidable relative to one another such that a surface of the body and a surface of the plunger selectively engage the tubing to pinch the tubing closed, the plunger sliding between a first, closed and occluding position wherein plunger pinches the tubing against the body and a second, open and non-occluding position wherein the plunger does not pinch the tubing closed, the plunger comprising a guide for selectively preventing the plunger from moving from the first, closed and occluding position into the second, open and non-occluding position;
a biasing member for biasing the plunger into the first, closed and occluding position; and
wherein the guide comprises a catch which engages the body to prevent movement of the plunger from the first, closed and occluding position into the second, open and non-occluding position unless the catch is moved;
wherein the guide has a projection which extends into an opening in the body and wherein pressing on the projection moves the guide away from the body to thereby allow the catch to disengage the body sufficiently to enable movement of the plunger into the second, open and non-occluding position.

20. A fluid delivery set comprising:
a tubing
a body and a plunger slidable relative to one another such that a surface of the body and a surface of the plunger selectively engage the tubing to pinch the tubing closed, the plunger sliding between a first, closed and occluding position wherein plunger pinches the tubing against the body and a second, open and non-occluding position wherein the plunger does not pinch the tubing closed, the plunger comprising a guide for selectively preventing the plunger from moving from the first, closed and occluding position into the second, open and non-occluding position;
a biasing member for biasing the plunger into the first, closed and occluding position; and
wherein the guide comprises a catch which engages the body to prevent movement of the plunger from the first, closed and occluding position into the second, open and non-occluding position unless the catch is moved;
wherein the plunger comprises a second guide, and wherein the two guides center the plunger in the body.

21. The fluid delivery set of claim 20, wherein both guides comprise a catch which selectively engages the body to selectively prevent the plunger from being moved from the first closed and occluding position to the second, open and non-occluding position.

22. The fluid delivery set of claim 21, wherein the body comprises openings and wherein the guides further comprise projections which extend into the openings in the body and wherein pressing the projections inwardly disengages the catches from the body sufficiently to allow the plunger to be pushed into the second, open and non-occluding position.

23. The fluid delivery set of claim 22, wherein the biasing member returns the plunger to the first, closed and occluding position unless an external force is applied thereto.

24. The fluid delivery set of claim 22, further comprising a pin insertable into an opening in the body to hold the plunger in the second, open and non-occluding position.

* * * * *